(12) United States Patent
Pullammanappallil et al.

(10) Patent No.: US 8,962,310 B2
(45) Date of Patent: Feb. 24, 2015

(54) SYSTEM FOR ANAEROBIC DIGESTION OF SOLID AND SOLUBLE ORGANIC WASTES, BY-PRODUCTS AND RESIDUES

(71) Applicant: University of Florida Research Foundation, Inc., Gainesville, FL (US)

(72) Inventors: Pratap Pullammanappallil, Gainesville, FL (US); Kerry Johanson, Gainesville, FL (US); Ioannis Martinos Polematidis, Jacksonville, FL (US); John M. Owens, Brunswick, GA (US); David P. Chynoweth, Gainesville, FL (US)

(73) Assignee: University of Florida Reearch Foundation, Inc., Gainesville, FL (US)

( * ) Notice: Subject to any disclaimer, the term of this patent is extended or adjusted under 35 U.S.C. 154(b) by 56 days.

(21) Appl. No.: 13/803,218

(22) Filed: Mar. 14, 2013

(65) Prior Publication Data
US 2013/0288326 A1    Oct. 31, 2013

Related U.S. Application Data

(60) Provisional application No. 61/638,652, filed on Apr. 26, 2012.

(51) Int. Cl.
*C12M 3/00*    (2006.01)
*C12M 1/00*    (2006.01)
(Continued)

(52) U.S. Cl.
CPC .............. *C12M 21/04* (2013.01); *C12M 21/16* (2013.01); *C12M 23/58* (2013.01); *C12M 27/20* (2013.01); *Y02E 50/343* (2013.01)
USPC .................. 435/299.1; 435/289.1; 435/299.2; 435/298.1; 435/304.1; 435/304.2

(58) Field of Classification Search
CPC ...... C12M 21/04; C12M 27/18; C12M 27/22; C12M 27/20; C12M 29/04; C12M 29/26; C12M 33/14
USPC .......... 435/289.1, 298.1, 299.1, 304.1, 304.2, 435/299.2
See application file for complete search history.

(56) References Cited

U.S. PATENT DOCUMENTS 4,446,018 A  *  5/1984  Cerwick ..................... 210/195.4
5,045,470 A  *  9/1991  Kloss ......................... 435/297.2

(Continued)

FOREIGN PATENT DOCUMENTS

EP            2386648 A1    11/2011
JP         2007-289946 A    11/2007
WO    WO-2012/011802 A2     1/2012

*Primary Examiner* — Nathan Bowers
(74) *Attorney, Agent, or Firm* — Saliwanchik, Lloyd & Eisenchenk

(57) ABSTRACT

The subject invention provides advantageous systems and processes for anaerobic digestion of organic waste streams, particularly agricultural waste streams. According to this invention, a new process is provided in which a liquid fraction from an organic waste stream comprising soluble compounds is segregated and incubated in a reactor separate from the solids fraction of the organic waste stream. Digestion of waste in both reactors occurs substantially simultaneously and both reactors produce biogas (thus both reactors function essentially like single stage reactors but allow for continuous or intermittent loading). According to one aspect of the invention, at least one cross-flow baffle is provided for use in an anaerobic digester to collect biogas and break up clumped solids in the reactor. In another aspect of the invention, packing media for use in an anaerobic digester is provided.

34 Claims, 16 Drawing Sheets

(51) Int. Cl.
*C12M 1/107* (2006.01)
*C12M 1/16* (2006.01)

(56) References Cited

U.S. PATENT DOCUMENTS

| | | | |
|---|---|---|---|
| 5,389,258 A * | 2/1995 | Smis et al. | 210/603 |
| 5,500,118 A * | 3/1996 | Coenen et al. | 210/603 |
| 6,929,745 B2 * | 8/2005 | Verink | 210/603 |
| 2002/0000409 A1 * | 1/2002 | Lanting et al. | 210/603 |
| 2003/0034300 A1 * | 2/2003 | Srinivasan et al. | 210/610 |
| 2007/0151916 A1 * | 7/2007 | Knappe et al. | 210/321.74 |
| 2008/0302726 A1 * | 12/2008 | Moller et al. | 210/661 |
| 2010/0015679 A1 | 1/2010 | Konwinski et al. | |
| 2011/0136213 A1 | 6/2011 | Stewart | |
| 2013/0264282 A1 * | 10/2013 | Chen et al. | 210/605 |

* cited by examiner

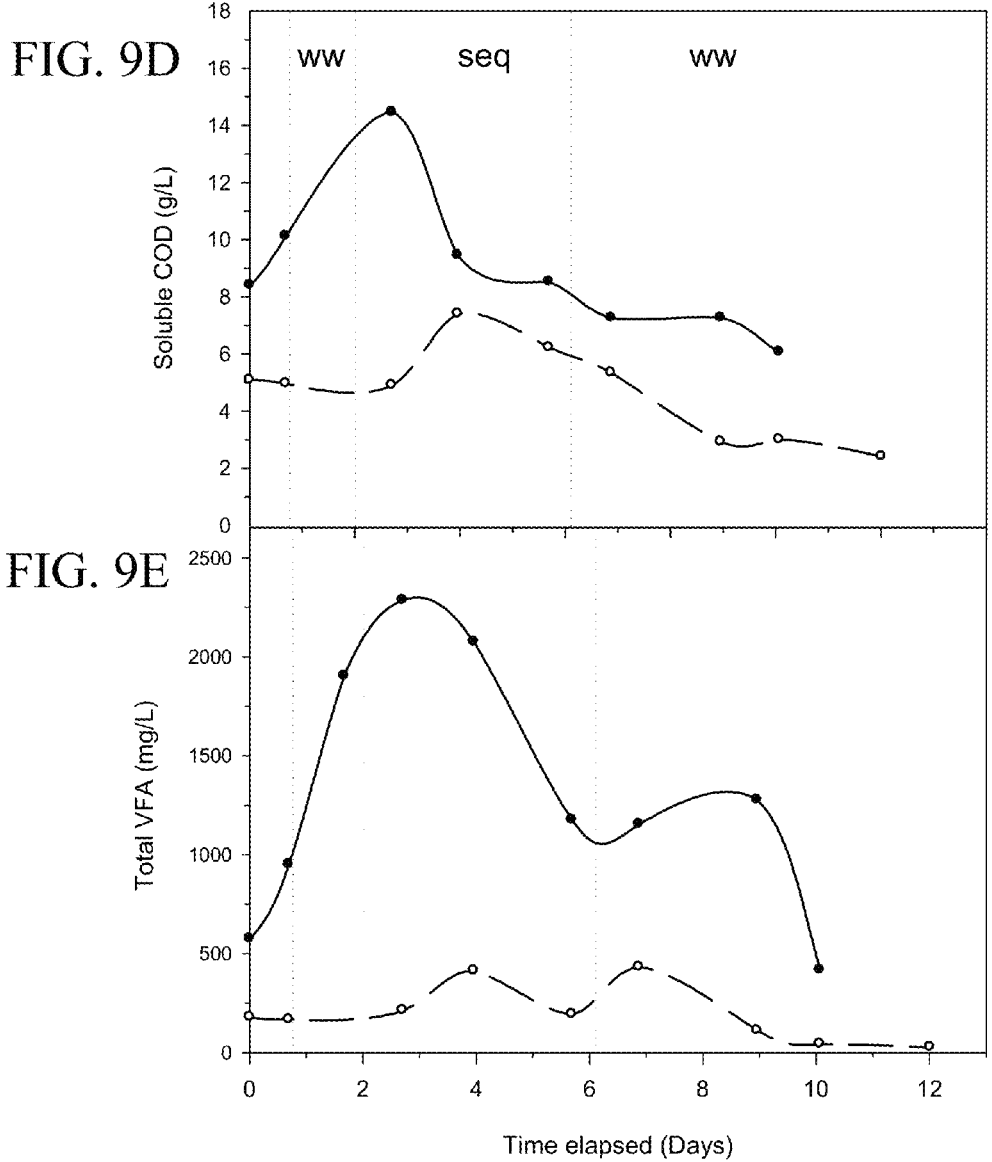

——•—— ABCR: Exp IV.2
——∘—— AFR: Exp IV.2

FIG. 11A
FIG. 11B
FIG. 11C
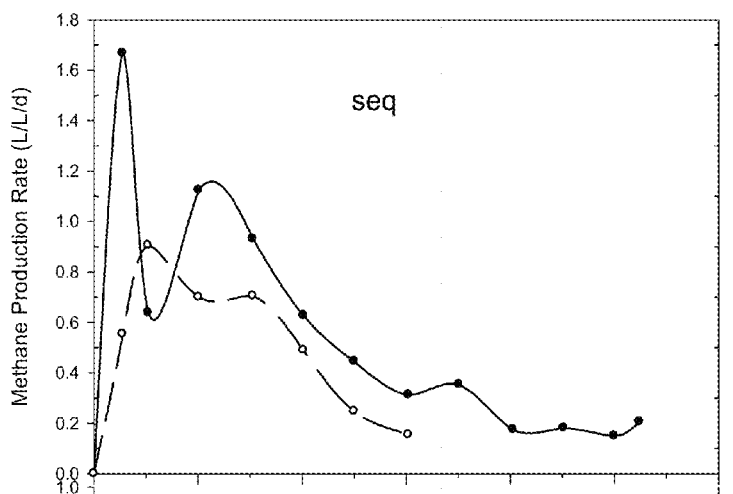
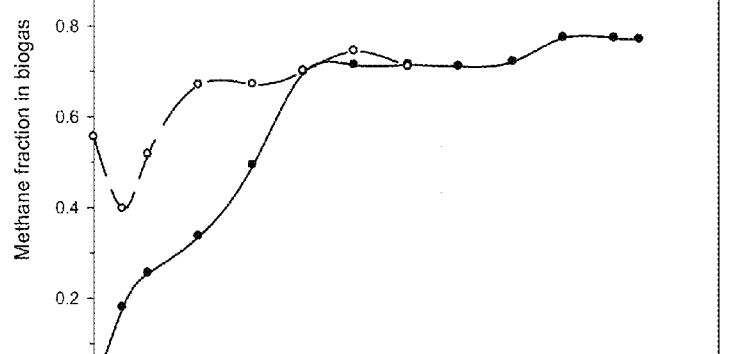
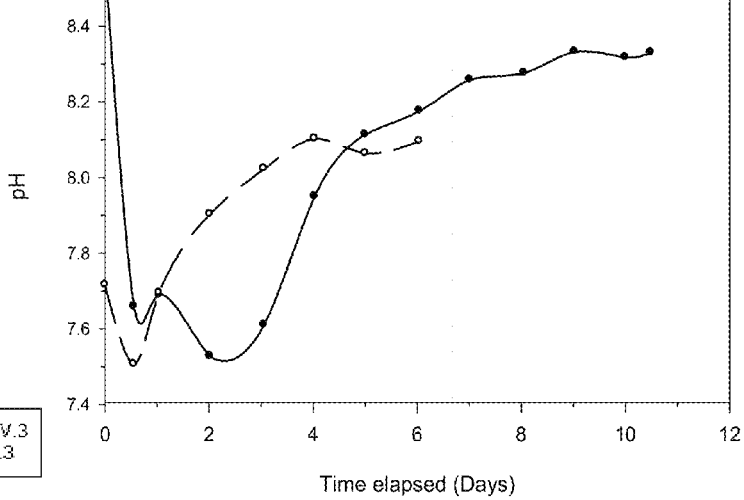

———•——— ABCR: Exp IV.4
———○——— AFR: Exp IV.4

SYSTEM FOR ANAEROBIC DIGESTION OF SOLID AND SOLUBLE ORGANIC WASTES, BY-PRODUCTS AND RESIDUES

CROSS-REFERENCE TO A RELATED APPLICATION

This application claims the benefit of U.S. provisional application Ser. No. 61/638,652, filed Apr. 26, 2012, which is incorporated herein by reference in its entirety.

GOVERNMENT SUPPORT

The subject invention was made with government support under a research project supported by the National Aeronautics and Space Administration, Contract No. NCC 9-110. The government has certain rights to this invention.

BACKGROUND OF THE INVENTION

Many approaches for waste disposal are currently available. For example, sanitary landfills formed by filling a land area with successive layers of solid waste and layers of earth or soil are well known. Unfortunately, such landfills have the potential for producing large amounts of a hazardous, explosive gas (methane), which may migrate to buildings or structures several hundred feet from the landfill if not removed from the landfill. Further, when this gas escapes into the atmosphere, it is about twenty times more potent as a greenhouse gas as carbon dioxide, which can have significant negative environmental effects. The natural precipitation draining out of the landfill may carry toxic, polluted water to contaminate underground water supplies, surface streams, and wells. Due to the very slow stabilization of waste, a landfill may not be used for other purposes for long periods of time and, thus, particularly near metropolitan areas, represents a large waste of land.

Other approaches utilize anaerobic digestion for stabilization and conversion of organic wastes to methane and compost. Anaerobic digestion is a series of processes in which microorganisms degrade and convert organic material in the absence of oxygen to produce usable gas and substrate. As part of an integrated waste management system, anaerobic digestion reduces the emission of landfill gas into the atmosphere. Anaerobic digestion is widely used as a renewable energy source because the process produces a methane and carbon dioxide rich biogas suitable for energy production helping replace fossil fuels. Also, the nutrient-rich digestate (compost) can be used as fertilizer.

The designs and strategies employed to enhance anaerobic biogasification of organic feedstocks has been thoroughly researched in the last two decades. Among design options, each has its own set of benefits and constraints and the selection process is usually dependent upon feedstock characterizations and/or personal preference. Designs usually depend on factors such as reactor solids concentration, mixing strategy, temperature and number of stages (Chynoweth and Pullammanappallil, 1996, Anaerobic digestion of municipal solid wastes. In Palmisano, A. C. and Barlaz, M. A. eds. Microbiology of Solid Waste. CRC Press, Inc. Boca Raton, Fla., p. 71-113; Gunaseelan 1997, Anaerobic digestion of biomass for methane production: a review. Biomass and Bioenergy 13, 83-114; Mata-Alvarez and Llabres, 2000, Anaerobic digestion of organic solid wastes. An overview of research achievements and perspectives. Biores. Technol. 74, 3-16).

Single-stage anaerobic digestion (also known as one-phase system) involves a single housing in which the organic substrate and the microorganisms are contained. These systems are limited because they require continuous handling of feedstock (especially when total solids (TS) >20%). Moreover, there is little control over the reactions occurring in the system. The biogas produced in one phase systems consists primarily of carbon dioxide in the early stages of digestion, the high carbon dioxide content being attributable to the slow growth of the methanogenic microorganisms. The growth and proliferation of methanogenic microorganisms are further limited in single-stage systems as a result of high concentrations of volatile fatty acids (VFAs) due to hydrolysis and fermentation of macromolecules by acidogenic microorganisms. Thus, the biological reactions of different species in a single stage reactor can be in direct competition with each other. When the acidogenic and methanogenic processes are not synchronized, the entire system can shut down or the maximal methane gas yield is only achieved after longer retention times (Sarada and Joseph, 1995, A comparative study of single and two stage processes for methane production from tomato processing waste. Processing Biochemistry 31(4), 337-340).

In order to reduce the inhibition of methanogenic microorganisms by the high concentration of VFAs produced during acidogenesis, the two-phase digester has been introduced. Two-phase systems permit much higher organic substrate loads and have been proven to run at lower retention times than single-stage systems. FIG. 1 shows the block-flow diagram of a two-phase system (Azbar and Speece, 2001, Two-phase, two-stage and single-stage anaerobic process comparison. Journal of Environmental Engineering, March, 240-248). In literature, a "two phase system" and "two stage system" tend to be used interchangeably. For the purposes of this application, the two-phase and two-stage will be treated as separate processes.

A two-phase system refers to the optimization of different digestion vessels to bring maximum control over the bacterial communities living within the digesters. In this process, fermentation (acidogenic bacteria) and methanogenesis (methanogic bacteria) are performed in separate reactors and distinguished by using different retention times. Typically, hydrolysis, acetogenesis, and acidogenesis occur within the first reaction vessel. Methanogenesis occurs in the second vessel.

Solid organic material (biomass) is added to the first vessel so that the biomass can be broken down into smaller constituents by acidogenic bacteria. The digested organic material from the first vessel is then often heated to an optimal temperature for methanogenic breakdown and pumped into the second vessel. Most biogas from the anaerobic two-phase system is collected from the second vessel, although a small amount of biogas may be produced in the first vessel. Unfortunately, with existing two phase systems, there are higher operational and maintenance requirements than that of single phase systems. For example, time for digestion (also referred to as retention time) in two phase systems can be long. This is generally due to the need for retaining the organic material in the first vessel for a period of time prior to addition to the second vessel to allow for proper hydrolysis/acidogenesis. Further, because a large portion of biogas is produced in the second vessel, there is untapped potential in having the first vessel also produce useable biogas.

Further, some digester systems are batch systems (see, for example, process known as sequential batch anaerobic composting or SEBAC). With these systems, biomass is added to a reactor at the start of the process in a batch and is sealed for the duration of the digestion process. Unfortunately batch reactors often suffer from odor issues that can be a severe problem when the reactor is emptied. Moreover, depending on the fermenting material and temperature, gas production from a batch-feeding will begin after two to four weeks, gradually increase to a maximum output and then fall off after about three or four months. Thus, often two or more batch digesters must be used in combination so that at least one will always be producing gas. To address this issue, continuous digestion processes were developed. With continuous digestion, organic matter is constantly added, or added in stages, to the reactor. The end products are constantly or periodically removed, resulting in constant production of biogas.

A common operational problem associated with any anaerobic digestion system is "foaming" Foaming is the trapping of fine bubbles of gas in the semi-liquid digestion contents of a reactor. Foam forms primarily when the carbon dioxide-to-methane ratio is higher than normal. This usually occurs during start-up operations, but it can occur whenever a fresh food supply suddenly contacts live organisms. Currently, the only effective solution to dealing with this problem is to establish a two phase digester system.

Thus a system and method for more efficient anaerobic digestion of organic materials, particularly plant and crop wastes, that addressed the foaming issue and enabled greater production of usable biogas from both reactors in a two phase system would represent a significant advance. Quite surprisingly the present invention provides such systems and methods.

BRIEF SUMMARY OF THE INVENTION

In one aspect, the subject invention provides a novel approach to anaerobic digestion of solid waste, particularly yard and/or agricultural waste. The improved system and process employs a two phase system with sealable reactors that simultaneously and continuously process organic wastes, by-products or residues to produce a biogas. The system is preferably used for processing organic waste streams that are high in solids content and soluble organic compounds.

In a method of use, at least two reactors are operated in parallel. The first reactor of the system is devoted to the digestion of the solids derived from an organic waste stream (which can be provided from a second reactor). A second reactor of the system is a liquid reactor for digesting soluble organic compounds in wash water following pretreatment of an organic waste stream. Contrary to prior two-phase anaerobic processes, the first reactor does not require acidogenic bacteria (rather, the first reactor must be kept at a neutral pH) and does not need to be heated for methanogenic breakdown. Moreover, the solids added to the first reactor of the system do not require pre-treatment for proper digestion. Each reactor operates as a single phase digester where biochemically mediated reactions occur that continuously convert organic compounds to biogas for continuous digestion.

In one embodiment, to the first reactor, only the solid form of the agricultural waste-products is added with pH neutral liquid that can (or cannot) be inoculated with bacteria for waste breakdown. Acidified liquid waste produced from agricultural waste-products is preferably added to the second sealable reactor. Anaerobic digestion of the organic waste stream is conducted simultaneously in both reactors. In both reactors, gaseous effluent comprising preferably high levels of methane biogas are collected. In a preferred embodiment, sugar beet tailings are treated using the anaerobic digestion system and method of the invention.

According to the subject invention, the liquid product yields from both reactors are circulated between the two reactors. In one embodiment, liquid is periodically withdrawn from the first tank and pumped into the second tank. A level equalization line connects the two tanks maintaining the level between tanks. The second tank is also provided with a liquid overflow line to discharge excess liquid.

According to the subject invention, the separated organic waste stream (soluble organic compounds separated from the solids) is continuously or intermittently introduced into both the first liquid reactor and second solids reactor, where each reactor houses the microbial population species that best converts the organic substrate into useful biogas. In one embodiment, operation of one or both reactors is performed at mesophilic temperatures (from about 32°-40° C.) or thermophilic temperatures (from about 50°-58° C.). Preferably, operation of both reactors is performed at thermophilic temperatures from about 50°-55° C.

The design of the first and second sealable reactors depends on the nature of the feedstock that is to be introduced. If the feedstock consists of small particles (less than 1 cm in length or diameter) then the first reactor contains no agitators or mixing equipment or other attachments and the feedstock material is introduced into the bottom of the first vessel using a pump.

For those feedstocks that are made up of larger organic particles (up to about 1 in length or diameter) or longer fibers, the first reactor provides: (1) sealed entry of bulk material into the top or bottom, where access is provided to the solid and/or liquid (e.g., through a rotary valve or feeder); (2) vertical flow of bulk materials through the tank; (3) sealed egress of residual bulk materials (e.g., through a rotary valve or feeder) connected to a receiving hopper at the tank top or bottom; (4) a means to manage gas production and liquid exchange with the bulk materials.

Accordingly, in another aspect of the invention, an anaerobic digester is provided that includes at least one internal horizontally arranged baffle, which comprises a means to extract localized gas pockets and localized free liquid, and further to inject liquid (and/or gas) into the bulk materials. The baffle system is particularly advantageous in that the injection of liquid (and/or gas) into the bulk materials ensures continuous motion of materials within the digester for optimal exposure to bacterial digestion and wetting of materials.

In one embodiment, at least one baffle is disposed within the digester for bulk solid materials. Preferably, the solids digester comprises a plurality of baffles. Each baffle includes an elongated body having a top surface. The cross section of the baffle can be of any geometric shape. In certain embodiments, at least a portion of the top surface is arched or tented. The elongated body of a baffle is oriented substantially horizontally within the digester. Where there is a plurality of baffles, each is vertically and horizontally spaced apart so that the bulk solid material that moves within the chamber of the digester is horizontally displaced as the solid materials pass by the baffles.

In a preferred embodiment, the baffle cross sections are of an inverted tee-pee shape to allow bulk solid materials to freely flow around the horizontal obstructions while moving down the digester tank. In another embodiment in which a plurality of baffles is provided, horizontal rows of baffles are offset from adjacent rows. According to the subject invention, the spacing of baffles, vertically and horizontally is chosen based on the permeability of surrounding bulk materials, rheological properties, the need to extract or add liquids to these materials, and the need to extract or add gases to these materials.

The anaerobic digester in which at least one horizontally arranged baffle is positioned can be any available conventional single-stage anaerobic digester useful in processing solid wastes. In certain embodiments, the anaerobic digester is one of common and/or commercial design used for treating wastewater containing soluble feedstock. These designs include anaerobic filter (downflow or upflow stationary or fixed film), upflow anaerobic sludge blanket reactor, fluidized bed reactor, and the like.

In another aspect of the invention, a unique packing media is provided for placement in an anaerobic digester tank for use in immobilizing bacteria, preventing washout of slower growing bacteria cells, and providing biomass retention independent of hydraulic retention time. With the subject media, more bacteria are available for a given reactor volume as compared to conventional anaerobic digesters and less time is needed to degrade the waste, allowing operation at short hydraulic retention times. An advantage of this media is that it does not clog like other heavy packing material.

In one embodiment, the media is a porous material capable of supporting bacteria on the surface of the media. It may be of any material that provides support to bacterial colonies, including any one or combination of rubber, plastic, wood, rock, including lava rock, activated carbon, expanded clay, tire chips, fabrics, including synthetic fabrics, coal, stone, or metal. The pores of the media should be of sufficient size, shape, and configuration so as to not inhibit to any great degree fluid movement through the media. The media should have the characteristic of being able to slough the microbial growth at such an interval and in such a way so as to not prevent the fluid movement through the media.

In a preferred embodiment, the media is non-oriented media that is constructed from semi-rigid, high-density polyethylene plastic mesh sheets (approximate mesh size 1 to 2×2 inch). This material is lightweight, inexpensive and resistant to harsh environmental conditions and non-corrosive. The media material can be easily transported and stored as rolls.

In one embodiment, the media comprises at least one 4 ft×4 ft polyethylene plastic mesh sheet that is bundled and the bundle is held together by cable ties. In another embodiment, the media comprises several bundles of the mesh sheet held together by cable ties. Since the media tended to float, these were tethered to the bottom screen plate of the digester by a nylon rope. The nylon ropes were of different lengths, allowing the media to fill the entire digester.

In yet another embodiment of the invention, the first reactor further comprises a bulking agent to assist in ensuring distribution of solid materials and reduce solid material compaction as well as increase porosity for better liquid and gas movement within the digester. Preferably, the bulking agent is a material that is robust and inert and of sufficient size and weight to sink slowly from the top of a digester to the bottom of a digester while redistributing the placement of solid materials within the digester.

BRIEF DESCRIPTION OF THE DRAWINGS

FIGS. 9a-9e are graphical illustrations of various observations derived from the operation of an embodiment of the two-stage sequential batch anaerobic composting system of the invention.

FIGS. 11a-11e are graphical illustrations of various observations derived from the operation of yet another embodiment of the two-stage sequential batch anaerobic composting system of the invention.

DETAILED DESCRIPTION OF THE INVENTION

Abbreviations and Definitions

SD refers to a single-stage anaerobic reactor for treating solids from an organic waste stream.

AFR refers to a single-stage anaerobic filter reactor for treating soluble components in waste water separated from an organic waste stream.

$CH_4$ refers to methane.

COD refers to chemical oxygen demand.

HRT refers to hydraulic retention time.

OFMSW refers to organic fraction of municipal solid waste.

SCOD refers to soluble chemical oxygen demand.

SEBAC refers to sequential batch anaerobic composting.

SRT refers to solids retention time.

TS refers to total solids.

VFA refers to volatile fatty acid.

VS refers to volatile solids.

As used herein, the term "organic substrate" refers to carbonaceous feedstock that can be used in the process and device of the invention to produce gas (such as methane, hydrogen, and carbon dioxide) and compost/fertilizer.

The terms "biogasification" and "methanogenesis" are used herein essentially interchangeably.

Figure 1:
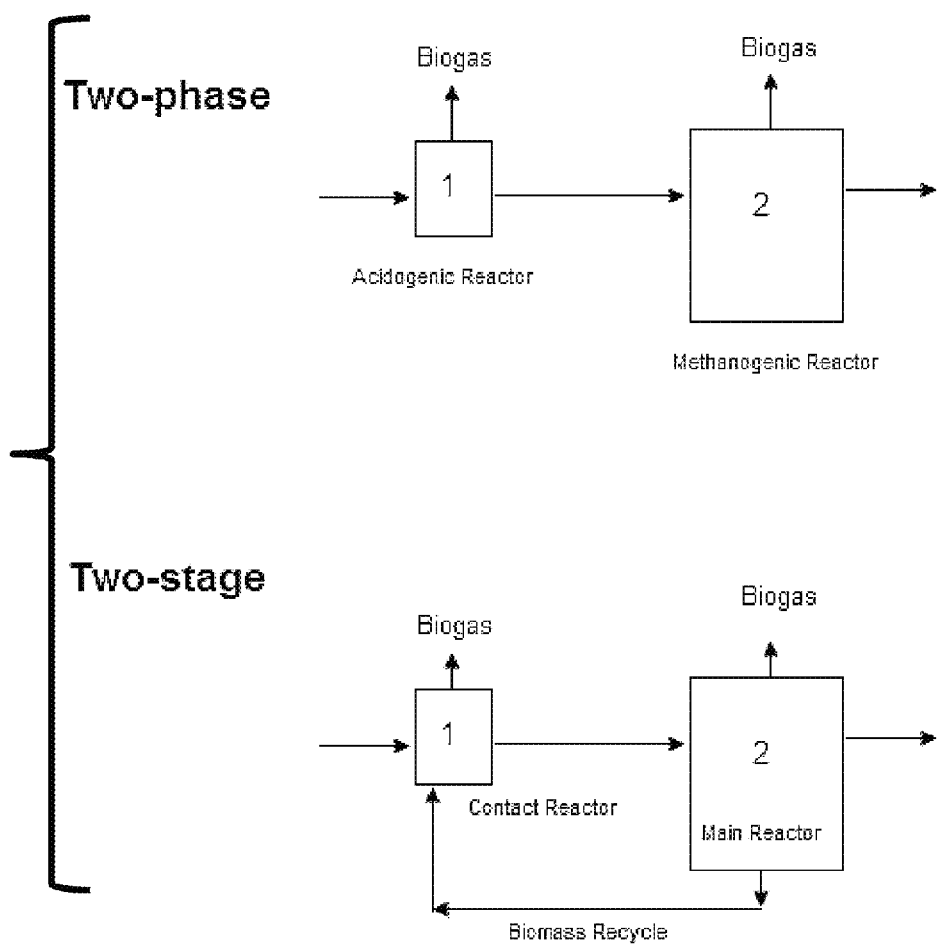
FIG. 1 illustrates the difference between a two-phase anaerobic digestion system and a two-stage sequential batch anaerobic composting system of the subject invention.

The subject invention provides a new system and process for two-stage digestion of wastes. As illustrated in FIG. 1, prior two-phase systems used a first acidogentic reactor that produced little biogas and a second methanogenic reactor that produced a large portion of useable biogas from the anaerobic system. The prior two-phase systems require pretreatment of waste prior to transfer into a reactor. Pretreatment normally involves segregating inert and bulky materials from the organic fraction of waste; reducing size of feedstock to provide uniform small size feedstock particles; and mixing waste with other substrates into a desired consistency. Following pretreatment, the solid organic wastes are transferred into a first acidogenic reactor and incubated under anaerobic conditions to produce a liquid component with volatile fatty acids and other compounds. The first acidogenic reactor generally produces insignificant amounts of biogas due to inhibition of methanogenesis as a result of acidic conditions within the first reactor. The resultant liquid component from the first reactor is then transferred to a second methanogenic reactor and incubated to produce appreciable amounts of collectable biogas.

In contrast to prior two-phase systems, the present invention provides a two-stage system in which organic wastes are separated into a solids fraction and liquid fraction having soluble organic compounds prior to transfer into separate reactors (FIG. 1). According to the subject invention, the solid waste materials would not require pretreatment prior to transfer into a reactor. Essentially, the solid fraction would not require reduction of feedstock size to provide uniform feedstock particles. The solids fraction can comprise less than about 55% total solid waste, from about 30% to 55% total solids (TS), more preferably between 35% to 50% TS, and even more preferably between 35% to 40% TS. In certain embodiments, the solid waste stream comprises about 20% to about 35% TS.

The subject two-stage system employs a liquid reactor (AFR) and a solids reactor (SD), wherein both reactors produce appreciable amounts of biogas. Preferably, the SD includes cross-flow baffles and/or bulking agents to assist in biogas collection, prevent compaction and flotation of solids and agitating the solids suspended in the reactor.

Initially, both solids to be digested and a liquid are added to SD. Thereafter, the liquid component consisting of soluble compounds from the organic waste stream is separated from the solids. The liquid component is transferred to an AFR and the solids are left in the SD. The process further comprises incubating the wastes in the SD and AFR substantially simultaneously under anaerobic conditions. After a first period of incubation, a portion of the liquid component from the SD is transferred into the AFR and a portion of the liquid component from the AFR is transferred into the SD. In certain embodiments, both the AFR and SD reactors have a level equalization line that maintains the level of liquid between the two tanks. In one embodiment, the AFR tank is also provided with a liquid overflow line to discharge excess liquid.

In the two stage process, an organic waste stream is separated into soluble organic compounds and solids. The liquid fraction comprising the soluble organic compounds preferably contains less than 2% total solids (TS).

The soluble organic compounds are transferred into at least one AFR and the solids are transferred into at least one SD. In one embodiment, transfer of compounds is performed at a controlled rate.

According to the subject invention, loading of the SD and AFR can occur substantially simultaneously initially.

According to the subject invention, the pH level in the SD and/or AFR reactors lies between about 6 to 8.5. More preferably, the pH level in the SD and/or AFR reactor(s) lies between about 6.5 to 7.5. Even more preferably, the pH level in the SD and/or AFR reactor(s) lies between about 6.8 to 7.0.

As understood by the skilled artisan, temperature affects survival and growth of microorganisms and it also influences their metabolic activities. According to the subject invention, the SD and/or AFR reactors can be operated at mesophilic temperature ranges or thermophilic temperature ranges. Preferred mesophilic ranges are about 20°-40° C. and preferred thermophilic ranges are about 50°-65° C. Even more preferably, the SD and/or AFR reactors are operated at either mesophilic temperatures between 35°-40° C. or thermophilic temperatures between about 50°-55° C. Should the SD and/or AFR reactors require heating, this can be accomplished using any variety of conventional sources. Contemplated sources for controlling the temperature of the digester include, for example, a solar water heater, a gas-powered water heater, a steam generator, a heater, a heat generator, and/or a heat exchanger.

The process of the invention can be practiced with any carbonaceous organic waste stream high in degradable waste solids content and containing soluble organic compounds. The carbonaceous organic waste stream can include, but is not limited to, sewage sludge, forestry waste, food waste, agricultural waste, municipal waste, yard/garden waste and the like.

In one embodiment, the organic substrate is selected from municipal waste, yard/garden waste, and/or agricultural waste. Yard/garden waste is any putrescible material such as leaves, grass clippings, yard trimming waste, perennial and annual plant materials, tree and shrub branches, other woody wastes such as wood chips, and the like. Municipal waste includes everyday items that are consumed and discarded including, for example, food wastes, hair, containers and product packaging, plastics, cardboard, paper, sewage, sludge, thickened sludge, and other miscellaneous organic and inorganic wastes from residential, commercial, and institutional sources.

In one embodiment, the organic waste stream consists, at least in part, of an agricultural waste. Agricultural wastes include plant and/or animal wastes, such as animal bedding, fur, sawdust and biosolids. Many types of agricultural waste can be used in conjunction with the subject invention. Useful agricultural wastes include, but are not limited to, foliage, straw, husks, fruit, vegetables, manure, and the like.

Figure 2:
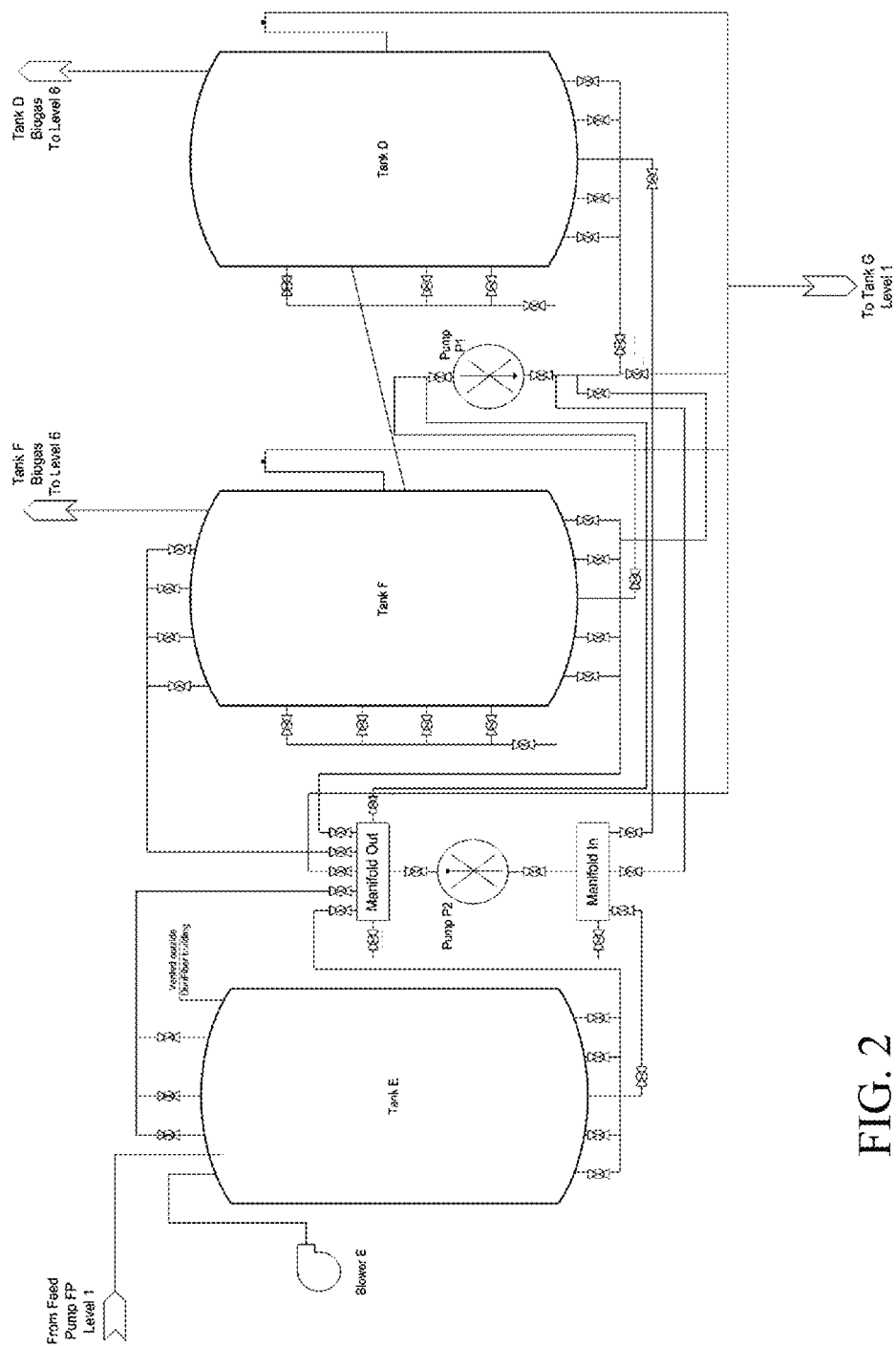
FIG. 2 illustrates one embodiment of the invention, wherein three single-stage reactors are used in two-stage sequential batch anaerobic composting in accordance with the subject invention.

FIG. 2 illustrates an embodiment of the invention in which the two-stage system comprises: a feed storage tank (Tank E); a first solids/SD reactor (Tank F), and a second liquid /AFR reactor (TANK D). In this system, Pump 1 pumps liquid between F and D. Pump 2 pumps feed slurry from storage tank E into bottom of Tank F. The design of Tank E depends on the nature of the feedstock that is to be introduced in aqueous form. Solids can also be introduced directly into SD using a rotary valve arrangement or through sealable chambers.

According to the subject invention, the AFR reactor can be a single tank or a series of tanks that receive the liquid fraction with soluble organic compounds. In addition, the SD reactor can be a single tank or a series of tanks that receive the solids fraction. Operation of the AFR and/or SD tanks produce at least one useful gas, such as methane, hydrogen and/or carbon dioxide. The hydraulic retention time (HRT) of the SD and AFR reactors may be approximately 12 hours to 12 days, depending on the velocity of conversion of the waste into biogas.

If the feedstock consists of small particles (less than 1 cm in length or diameter) then material from Tank E is introduced into the bottom of the SD using a pump.

For those feedstocks that are made up of larger organic particles or longer fibers, SD comprises: (1) sealed entry of bulk material, including solids waste fraction and bulking agents, into the top; (2) downward vertical flow of bulk materials through the tank; (3) sealed egress of residual bulk materials at the tank bottom; (4) a means to manage gas production and liquid exchange with the bulk materials through internal horizontally, or slightly angled, arranged baffles, which comprise a means to extract localized gas pockets, localized free liquid, and further to inject liquid into the bulk materials; (5) baffle cross sections that are of an inverted tee-pee shape (or other geometric configuration) to allow bulk materials to freely flow around the horizontal obstructions while moving down the tank; (6) horizontal rows of baffles that are offset from adjacent rows; and (7) spacing of baffles, vertically and horizontally based on the permeability of surrounding bulk materials, rheological properties, the need to extract or add liquids to these materials, and the need to extract or add gases to these materials.

In one embodiment, sealed entry and egress of bulk solid materials from the digester is provided with a rotary valve arrangement. This is particularly important in a continuous system in which solids materials need to be continuously added to the digester, which needs to maintain an anaerobic environment therein to ensure proper waste digestion. The rotary valve arrangement operates to selectively deliver bulk material into and out of the digester while preventing the release of solids or liquids from the digester and entrance of air into the digester. That is, the rotary valve arrangement provides a rotatable seal between the digester and the atmosphere. Rotary valves arrangements are well known to those skilled in the art and are not further disclosed herein. Contemplated rotary valve arrangements include, but are not limited to, rotary valves, staged valves, rotary lobe pumps, and/or other positive displacement pumps. A rotary valve of the invention may be operated at varying rates in order to increase or decrease the flow of feed material into and out of the digester.

In another embodiment, sealed entry and egress of bulk solid materials from a digester of the invention comprises a series of slotted grates that selectively slide between an open and closed position. The slotted grates bound at least one compartment. During operation a first grate opens allowing the bulk solid material to pass into a compartment through the slots. Once a desired amount of bulk solid material has entered the compartment, the first grate closes. The second gate then opens allowing the bulk solid material to travel from the compartment to or out of the digester. Once the compartment is empty, the second grate closes and the first grate opens again allowing the bulk solid material to enter the compartment. The grates can be operated at such a rate that the desired bulk solid material flow rate is maintained. Other embodiments of such elements (such as rotary lobe pumps) that perform analogous functions are contemplated within the scope of this invention. Other locations for the sealed ingress and egress that perform analogous functions are contemplated within the scope of this invention. For example, sealed entry and/or egress can be located at the top, bottom, or any portion of a side of the digester.

The second reactor (Tank D) is any available conventional single-stage anaerobic digester useful in processing solid wastes. In certain embodiments, the second reactor is one of common and/or commercial design used for treating wastewater containing soluble feedstock. These designs include anaerobic filter (downflow or upflow stationary fixed film), upflow anaerobic sludge blanket reactor, fluidized bed reactor, and the like.

Periodically liquid is withdrawn from the first tank (such as Tank F) and pumped into the second tank (such as Tank D). A level equalization line connects the two tanks maintaining the level between tanks. The second tank (such as Tank D) is also provided with a liquid overflow line to discharge excess liquid.

In certain embodiments, a bulking agent is added to the SD digester to assist in ensuring distribution of solid materials and reduce solid material compaction as well as increase porosity for better liquid and gas movement within the digester. Preferably, the bulking agent is a material that is robust and inert and of sufficient size and weight to sink slowly from the top of a digester to the bottom of a digester while redistributing the placement of solid materials within the digester. Contemplated bulking agents include coal, stones, gravels, rocks, including lava rock, metal objects, plastic materials, yard trimming waste, cardboard, expanded clay, wood chips, sawdust, animal bedding biosolids (e.g., pelletized sludge), hair, including animal hair, and other like materials.

Figure 3A:
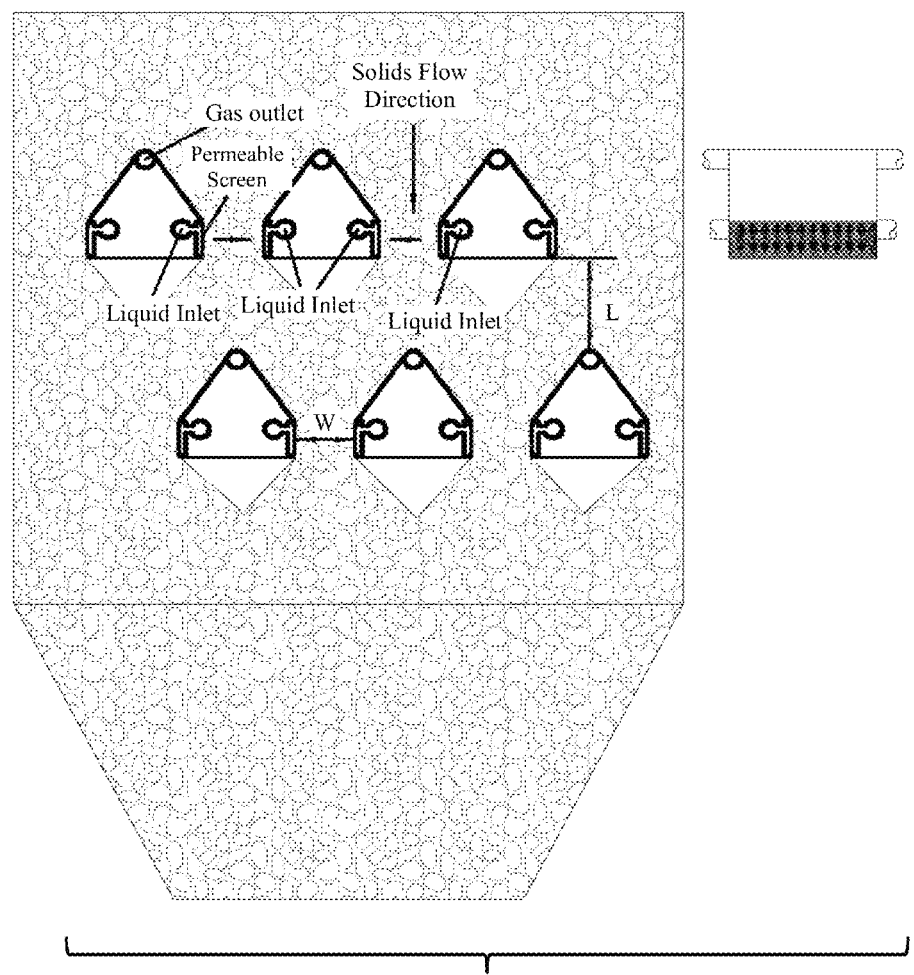
FIGS. 3A, 3B, and 3C illustrate internal horizontally arranged baffles located in the first reactor of the two-stage sequential batch anaerobic composting system of the invention.
Figure 3B:
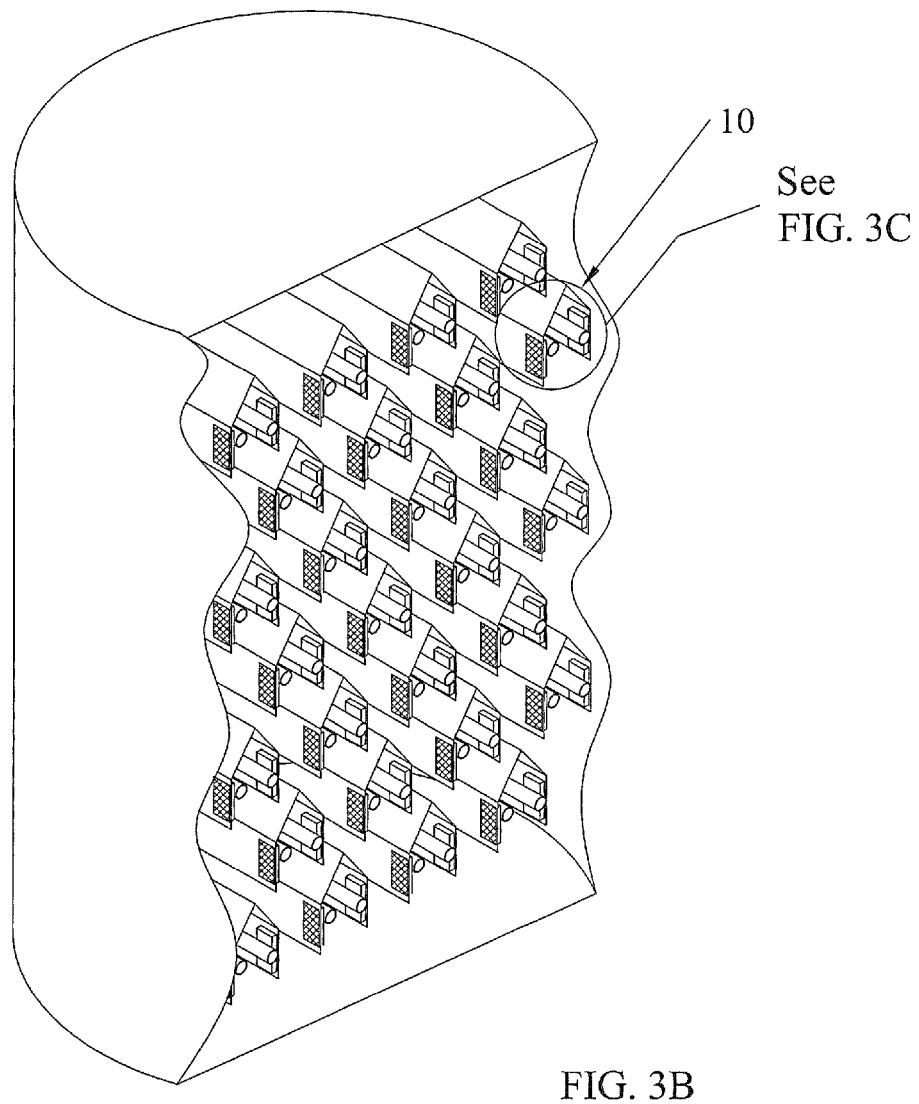
Figure 3C:
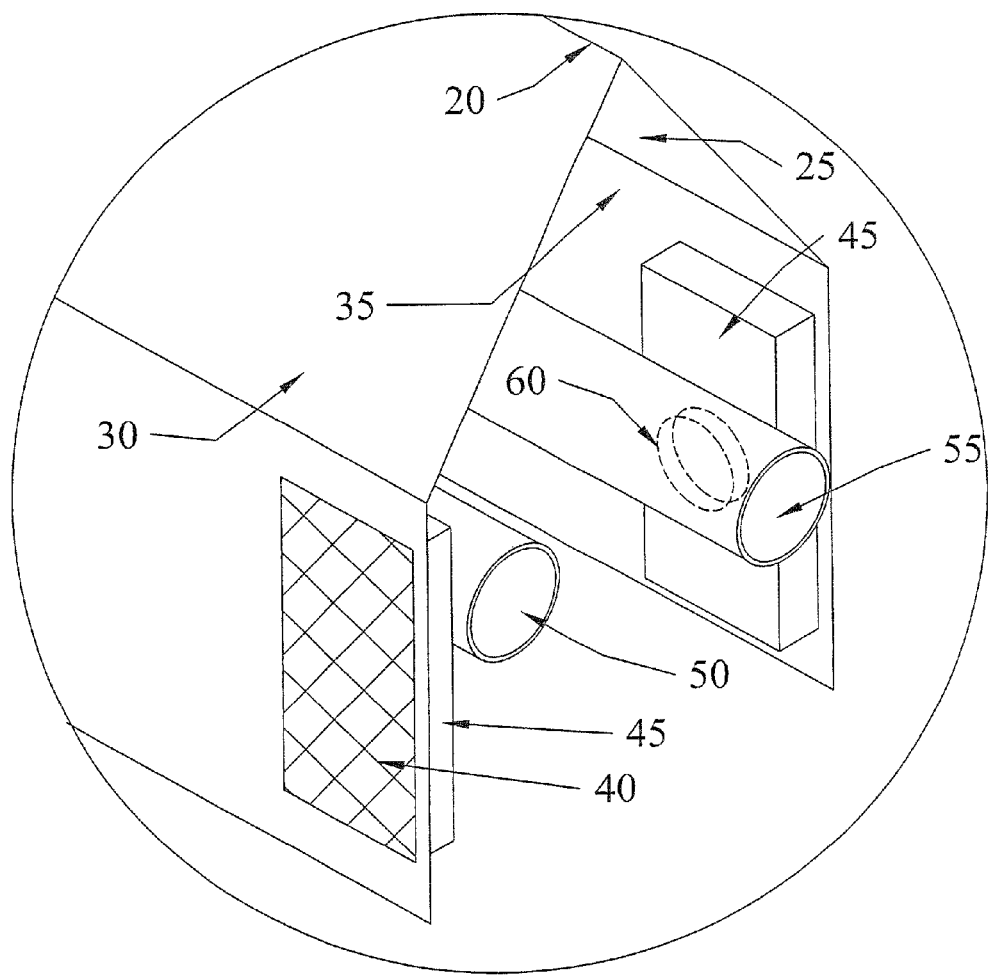

FIGS. 3A, 3B, and 3C are diagrams of the cross-flow baffles to be used in any of the anaerobic digesters of the invention (AFR or SD). According to the subject invention, at least one cross-flow baffle 10 is disposed within the SD reactor to inject or withdraw liquids or gasses in a cross flow or radial direction. Preferably, several baffles are used in a digester to create a flow channel across the entire cross-section of the reactor. The cross-flow baffles of the invention allow the disengaging of entrapped bio as into a gas storage cavity. The baffles provide a means of providing intimate controlled contact of liquid and bulk solids materials using cross flow principles while allowing gas generated during the contact process to be collected in void spaces. This will prevent compaction of solids. Bulk solids flow downward between the baffles. Preferably, the crossflow baffles are only provided in the upper quarter to a third of the SD.

Extending between the side walls of the digester so as to be horizontally oriented within the digester is an array of spaced apart baffles. Each baffle comprises an elongated body having an inverted substantially V-shaped transverse cross section. Each body has height h and width w each in a range between about 3 cm to about 100 cm. To form the inverted substantially V-shaped transverse cross section, the top surface 20 of the elongate body has a first top side face 25 and an opposing second top side face 30 that are each disposed in diverging planes so as to have a substantially inverted V- or U-shaped configuration. In one embodiment, each of the top side faces is disposed in a plane forming an inside angle a relative to the horizontal in a range between about 45° to about 85° with about 55° to about 75° being more common and about 63° being even more common to form an inverted V. The top side faces can also form an inside angle between the faces in a range between about 1° to about 70° with about 20° to about 60° being more common to form an inverted V.

Preferably, the top side faces 25, 30 intersect at a corner to ensure the bulk solid material moves down one of the top side faces as opposed to vertically stacking on top of the baffle. In one embodiment, the top side faces intersect on a narrow ridge that does not allow solid materials to stack on top of the baffle. In certain embodiments, the narrow ridge can be slightly rounded but should not be so rounded or flat as to cause the bulk solid material to vertically stack on top thereof.

The top, substantially inverted V- or U-shaped top surface functions in part to deflect the solid bulk material as it passes down through the digester so that the bulk solid material is maintained in a continuous and dynamic mixing flow. Although the top surface of a baffle can have a variety of different configurations, if the apex of the top surface becomes too flat, particles of bulk solid material can rest and stagnate thereon until they block the flow of the bulk solid material through the baffles.

Thus, preferably, the apex or ridge of the top surface of the baffle should be very narrow to force the bulk solid material to flow down the side faces, thereby eliminating stagnate particles. The extent to which a ridge at the top surface of a baffle can be rounded is dependent on a number of factors such as the size of the bulk solid material and the speed of the bulk solid material moving around within the digester. By way of example, in one embodiment, the ridge can have a radius of curvature that is less than four times the maximum diameter of the bulk solid material, more commonly less than twice the maximum diameter of the bulk solid material, and even more commonly less than the maximum diameter of the bulk solid material. In yet other embodiments, the radius of curvature of the ridge can be equal to or less than about 0.5 times the maximum diameter of the bulk solid material. Other dimensions can also be used.

The substantially inverted V-shaped transverse cross section partially bounds a gas collection channel 35 extending along the length of the elongate body of a baffle. The gas collection channel is configured in part to capture methanogenic gas emitted from anaerobic digestion of the bulk solid material that is released from the liquid cross-flow between the baffles. A port at the wall of the digester can be provided to access the gas collected at the gas collection channel. The digester can also include a conduit from the port to harvest useful gas, such as methane gas, hydrogen and/or carbon dioxide generated within the digester or an internal pipe/channel can vent the gas to the void space at the top of the digester. In certain embodiments, the gas collection channel can come in a variety of different configurations. For example, the gas collection channel can have an inverted substantially U-shaped configuration or can have any number of curved, circular, rounded, sloped, irregular, or combined surfaces that form a cupped or circular surface capable of capturing gas. In other embodiments, the digester can be operated under a vacuum, which will increase the partial pressure of the gas and draw the gas to the void space at the top of the digester.

In certain embodiments, the AFR reactor also includes an area for capturing gas (e.g., void space at the top of the digester). The AFR reactor can include a conduit from the gas capture area to harvest useful gas such as methane, hydrogen and/or carbon dioxide generated within the digester.

The liquid injection and/or withdrawal system of the cross-flow baffles (illustrated as liquid outlets in FIGS. 3A, 3B and 3C) are provided along the side walls of the elongate body of a baffle. Along the side walls of the elongate body of a baffle are areas that are permeable 40 to the liquid within the digester. Preferably, the side walls consist of porous or permeable materials or membranes. In one embodiment, the side walls of the elongate body of a baffle are of intermeshed porous/permeable material and within the baffle is a channel 45 to collect materials that enter via the permeable side wall. The size of the pores or mesh will be dependent on the solid material present in the digester and the desired flow rates of liquid. In a preferred embodiment, the size of the pores is up to 250 microns. Even more preferably, the mesh material has a pore size of approximately 100 microns.

The permeable material can be the same or different from that of the cross-flow baffle(s). The permeable material can be of rubber, plastic, including fiberglass, fabrics, including synthetic fabrics, hair, including animal hair, or metal. Preferably, the permeable material is a metal mesh material that has a pore size of approximately 100 microns.

The liquid injection and withdrawal system of the cross-flow baffles are provided at the permeable side wall areas via channels 50, 55 that run parallel the elongate body of a baffle. The system includes at least one, preferably more than one, fluid pump for pumping liquid into and out of the liquid injection and withdrawal channels of a cross-flow baffle. In one embodiment, liquid is injected and/or withdrawn from the cross-flow via intermittent openings 60 from the channel to the collection channel along the permeable side wall areas.

Where there is a plurality of baffles present, baffles operate in sequence to generate a cross flow fluid velocity through a down-flow solids velocity profile. Liquid is siphoned into one porous plate and discharged through an adjacent porous plate at a controlled velocity to ensure predominantly cross flow of liquid through the bulk material during solids discharge. Liquid counter-flow often fluidizes the bulk material in a process vessel creating poor contacting control. The radial or cross flow injection prevents unwanted fluidization velocities creating better fluid contact during continuous operation. The direction of fluid injection may be periodically reversed to back wash the porous plates and clear them of solid particles. Further, gasses may be injected through the liquid lines to periodically remove particulates from the screens.

The materials used for the baffles are chosen to withstand the operation of the digester. For example, the materials must be corrosion resistant and prevent biofilm build-up. Examples of materials that can be used for the baffles include metals, such as cast iron, iron alloys, stainless steel, beryllium, and beryllium alloys; ceramics; and polymers; or combinations thereof. Other materials having the desired properties can also be used.

Multiple levels of baffle inserts are placed in the process vessel each level with independent control of liquid flow control. The liquid control of successive level of liquid can impose a net downward or upward liquid flow. This liquid flow control will overcome local solids arching across adjacent inserts.

In a preferred embodiment, an anaerobic digester contains a series of pup-tent shaped cross-baffle inserts that reach across the diameter of the anaerobic digester vessel in the vertical section. The sloping sides of the insert are sealed at the top and allow the gas to accumulate in the interior cavity beneath the insert. Pipes attached to a port at the end of the insert where it meets the wall of the digester, near the top of the baffle, allow the gas to leave the system and be harvested. The vertical walls along the sides of the insert are permeable and made of porous metal plates. These plates draw liquid through them or push liquid through them depending on the mode of operation required by the system. For example, liquid is drawn from one plate and injected into an adjacent plate. The bulk solid will flow with the liquid stream and cause compaction against the permeable metal filter plate that draws the liquid in. This action opens up a void in the bulk material flow and the compaction of the material against the filter causes any gas trapped in the bulk material to dislodge and percolate upward, preferably into a cross-flow baffle for collection. There are several rows of inserts and the row of inserts above are positioned offset to the row below such that any gas dislodged from the pumping action will percolate and collect in the upper row of inserts.

The normal operation of these inserts is to draw liquid into one plate and push liquid through a second adjacent plate. After a prescribed time the liquid flow is reversed, allowing liquid to be pushed through the first outlet and drawn through the second. This causes the bulk solid material to collect alternately against each plate and facilitate gas bypass for the total cross-sectional area of the digester. Preferably, at least two inserts at a minimum of two levels in the digester (total of four) are provided in a digester to facilitate gas discharge and collection. These inserts do not need to be throughout the entire digester, but should be positioned where the biomass accumulates in the vessel.

One of the issues with biomass anaerobic digestion is the formation of zones where gas entrapped in the solid does not allow liquid containing microbes to permeate the bulk material. The subject invention addresses this issue. The subject cross-baffle inserts are designed to help dislodge the gas generated during the anaerobic digestion. The width of the gap between each set of inserts is set in accordance to the plane flow arching dimension of the particular biomass in a submerged state. Biomass has cohesive flow properties and particle interlock properties that cause particles to stick together. The unconfined yield strength of biomass in submerged conditions can be measured to determine the critical arching dimension that will cause arching using the following equation.

$$AI = W = \frac{1.1 * fc}{\gamma \cdot g - \frac{dP}{dz}}$$

where:
fc is the unconfined yield strength
γ is the bulk density
dP/dz is the fluid pressure gradient The cross-baffle insert spacing must be at least equal to W to accommodate the particular biomass. If the spacing is set then, and different biomasses with different unconfined yield strength are used in the design, then the fluid pressure gradient in the z-direction can be adjusted to maintain the W value to below that required for arch prevention. You will need to adjust the fluid gradient to cause the computed W to be lower than the insert spacing. This fluid control can be accomplished causing a net downward flow of fluid between two levels of inserts. In addition to the flow between cross-flow baffle inserts, an imbalance in flow from an insert can be induced by pushing flow into the material in the adjacent insert below. Normally the flow drawing fluid through an adjacent plate would match that being supplied by the neighboring plate. However, if the injection of fluid in the lower insert is less than that supplied, then the fluid will move downward and provide the required pressure drop to overcome arching. Thus, the system can be designed for a range of biomass materials and has some adjustment to avoid plugging. The following is a preferred operational procedure assuming several inserts as described above are arranged in several rows. The inserts will be numbered from one side of the digester and: (1) fill digester to above inserts with biomass and liquid; (2) induce flow from all odd number inserts (relative to one side of the bin) at the upper level and every other level in the digester (fluid flow should move toward even number inserts for five minutes); (3) stop fluid flow in the digester for 15 minutes and allow the solid within the digester to relax; (4) induce flow from all even number inserts (relative to one side of the bin) at the upper level and every other level in the digester (fluid flow should move toward odd number inserts for five minutes); and (5) repeat this procedure as required to facilitate gas release.

Following are examples that illustrate procedures for practicing the subject invention. These examples are provided for the purpose of illustration only and should not be construed as limiting. Thus, any and all variations that become evident as a result of the teachings herein or from the following example are contemplated to be within the scope of the present invention.

I. Study: Experiments IV.1 to IV.4

Figure 4:
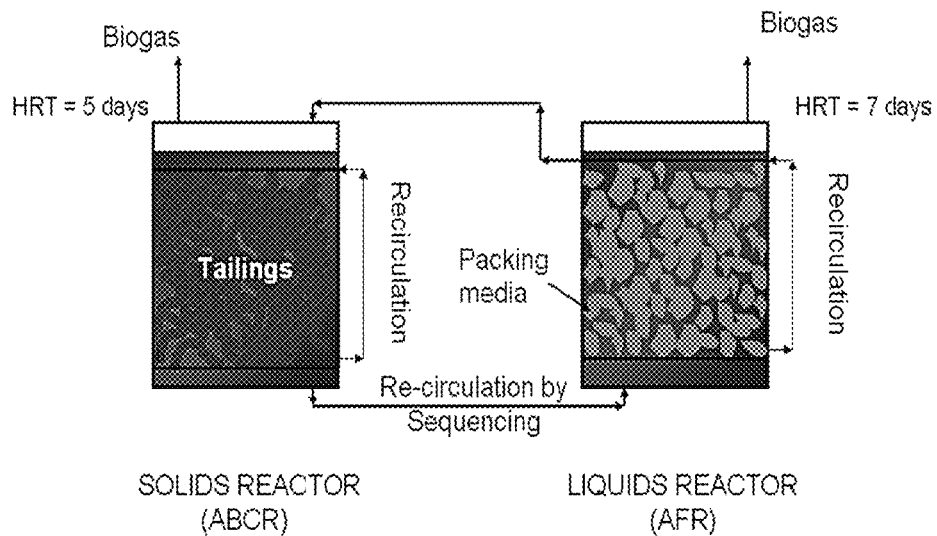
FIG. 4 illustrates another embodiment in which sugar beet tailings were introduced into a two-stage sequential anaerobic composting system of the invention.
Figure 5:
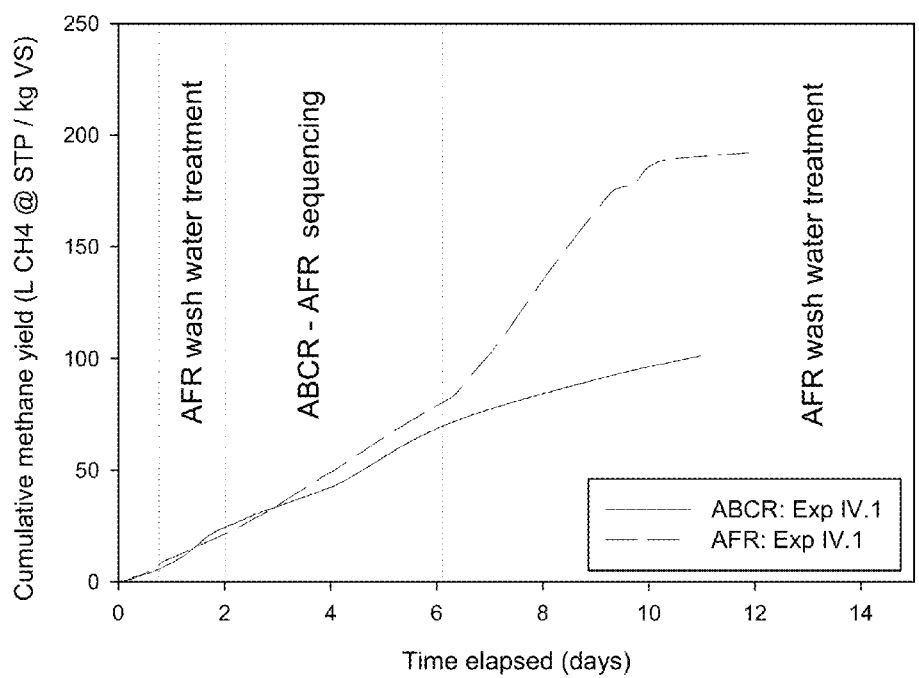
FIG. 5 is a graphical illustration of cumulative methane yields for the liquid and solid reactors used in an embodiment of the two-stage sequential batch anaerobic composting system of the invention.
Figure 6:
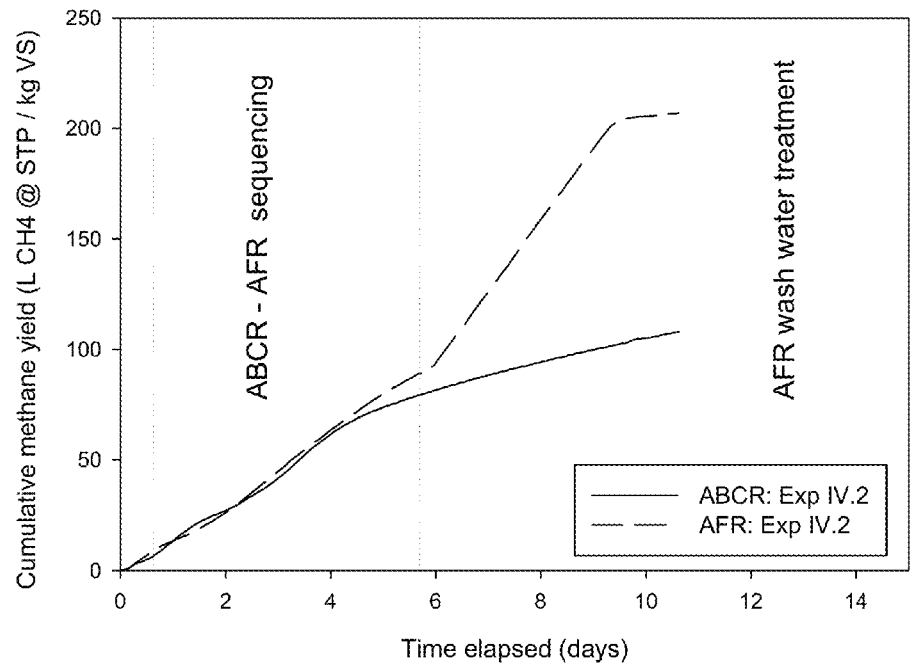
FIG. 6 is a graphical illustration of cumulative methane yields for the liquid and solid reactors used in another embodiment of the two-stage sequential batch anaerobic composting system of the invention.
Figure 7:
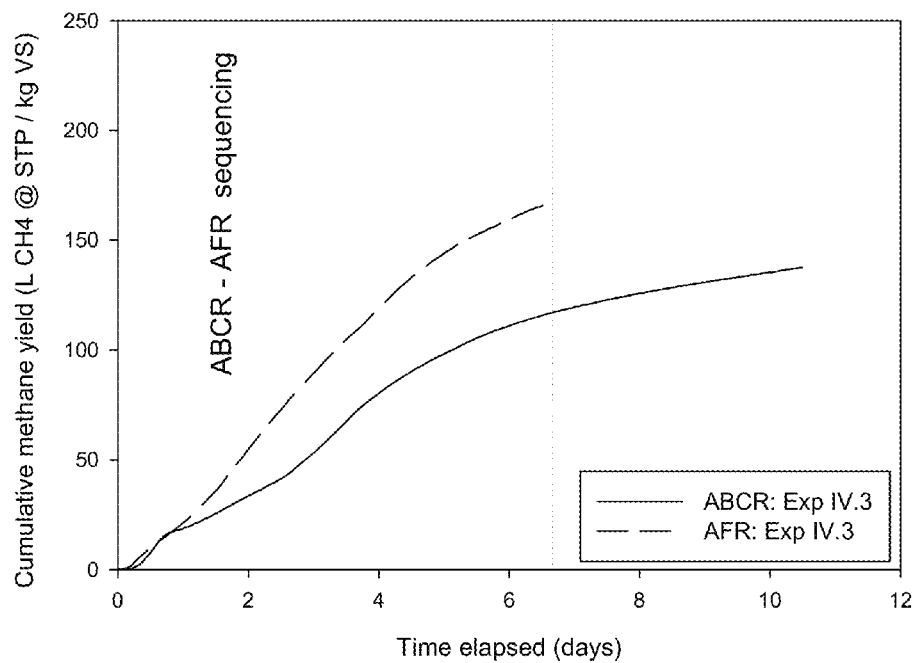
FIG. 7 is a graphical illustration of cumulative methane yields for the liquid and solid reactors used in yet another embodiment of the two-stage sequential batch anaerobic composting system of the invention.

A total of four experiments (IV.1 to IV.4) were conducted consecutively in a sequenced mode with the AFR, generally illustrated in FIG. 4. Sugar beet tailings in Experiments IV.1 and IV.2 were loaded in SD's and pre-treated exactly as un-bulked experiments. The AFR was used intermittently to process wash water generated from pre-treatment or sequenced with SD during the early stages of biogasification. Similarly, Experiment IV.3 was also loaded with 3-kg of raw sugar beet tailings, but in-situ pre-treatment to remove the readily soluble fraction was bypassed; biogasification and sequencing with the AFR were initiated immediately upon start-up. Experiments IV.1-IV.3 included bulking agents. Lastly, experiment IV.4 was conducted to demonstrate the utility of having an AFR when single-stage systems are overloaded.

The performance of each experiment in this Study was monitored by analysis of biogasification parameters. Sequencing between the AFR and SD was carried out until process performance (methane yield, % $CH_4$ composition, pH, decline if VFA concentration) in first stage (SD) showed improvements. Bicarbonate buffering was provided.

II. Characteristics of Feed and Digested Residue:

Table 1 lists the loading and unloading data for the experiments in this Study. The un-compacted packing density (dry basis) for all Experiments (IV.1 to IV.4) ranged between 75 to 100 kg/m$^3$. The visible volume usage for loading 3 and 5 kg of tailings in experiments was approximately half and three-quarters of the working volume (12 L), respectively. Upon loading raw tailings to digesters and flooding the TS concentration inside the 3 and 5 kg experiments were approximately 3.3 and 5.3% TS, respectively.

TABLE 1

Loading and unloading data for Experiments IV.1 to IV.4

| Experiments | | IV.1 to IV.3 | IV.4 |
|---|---|---|---|
| Loading | Wet tailings weight (kg) | 3 | 5 |
| | Total solids (kg) | 0.48 ± 0.02 | 0.77 |
| | Volatile solids (kg) | 0.43 ± 0.02 | 0.68 |
| | Inoculum added (L) | 12 | 10 |
| | Packing density (kg wet/m$^3$) | 470 | 490 |
| | Packing density (kg dry/m$^3$) | 97 ± 11 | 75 |
| | Total solids in reactor (%) | 3.3 ± 0.1 | 5.3 |
| Unloading | Wet residue weight (kg) | 0.93 ± 0.2 | 2.25 |
| | Total solids (kg) | 0.050 ± 0.01 | 0.088 |
| | Volatile solids (kg) | 0.05 ± 0.05 | 0.047 |
| | Total solids reduction (%) | 82 ± 2 | 86 |
| | Volatile solids reduction (%) | 88 ± 2 | 93 |

Residue samples from each experiment were unloaded and measured for TS and VS reduction. In opening reactors, it was observed that Experiment IV.4 had the highest visible volume reduction, approximately 80 to 90%; Experiments IV.1 to IV.3 were visually observed to have reduced between 70 to 80%. On average, TS and VS reduction for Experiments IV.1 to IV.3 were 82±2 and 88±2%, respectively; Experiment IV.4 yielded a TS reduction of 86% and VS reduction of 93%.

III. Physical Observations:

A rise of liquid in all four experiments due to displacement of liquid from generation of gas was observed during this Study. During sequencing with the AFR, the excluded liquid level in the SD reduced at a much faster rate than excluded liquid level in un-bulked runs. It was suspected that additional hydraulic injections and withdrawals due to sequencing promoted separation of accumulated biogas from the waste bed.

IV. Biogasification of Sugar Beet Tailings:

The cumulative methane yield profiles for the AFR and SD in Experiments IV.1 to IV.4 (FIGS. 5-8) were plotted together to highlight progression with respect to one another. The plots are also sectioned off to illustrate regions where AFR was either sequenced with an SD or used to treat wash water generated from pre-treatment. The abbreviations "ww" and "seq" (FIGS. 5-8) symbolize regions where wash water was being treated by the AFR and sequencing between the AFR and SD commenced, respectively. All un-marked regions indicated that both the AFR and SD were operating in a solo mode. The complete summary of operation times (Table 2), and experimental cumulative methane distributions (Table 3) was constructed as a basis for comparison between experiments.

The sequenced operation in Experiments IV.1 and IV.2 was implemented to address poor increases in methane rate and composition observed in unbulked treatments between days 4 to 6. Both Experiments IV.1 and IV.2 were operated in a two-stage sequenced operation for 4.1 and 5.1 days, respectively. The on-set of sequencing on the performance parameters of both the SD and AFR (FIGS. 9-12) was considered an important response factor. In general, methane production rate in the SD reactor was shown to improve by 0.4 to 0.6 L $L^{-1}$ $d^{-1}$ after a lag time (~2 days). The methane fraction in biogas showed dramatic increases, spanning from 25% to 55% within three days in both experiments. Similarly, the pH profiles exhibited in both SD and AFR showed increases at varying degrees; sequenced operation caused an increase from pH 7.8 to 8.1 in Experiment IV.1 and 7.2 to 8.1 in Experiment IV.2. The pH trends observed during the treat-

TABLE 2

Summary of operation times for two-stage experiments

| Experiment | Readily-solubilized fraction (g COD/g VS) | Wash time (Days) | Sequencing duration (Days) | Biogasification duration in SD (Days) | Biogasification duration in AFR (Days) | Sequencing HRT in SD (Days) | Sequencing HRT in AFR (Days) | Total process time (Days) |
|---|---|---|---|---|---|---|---|---|
| Two-stage | | | | | | | | |
| IV.1 | 0.51 | 0.5 | 4.1 | 10.9 | 12.0 | 5 | 7.5 | 12.5 |
| IV.2 | 0.50 | 0.5 | 5.1 | 10.6 | 10.6 | 5 | 7.5 | 11.1 |
| IV.3 | — | | 6.7 | 10.5 | 6.7 | 5 | 7.5 | 10.4 |
| [a]Single/Two-stage | | | | | | | | |
| IV.4 | — | — | 3.8 | 17.4 | 4.1 | 5 | 7.5 | 17.4 |

[a]Refers to recovery operation of a single-stage unit sequenced with the AFR

TABLE 3

Summary of cumulative methane yield distribution in two-stage biogasification

| Experiment | SD Cumulative Methane Yield (L CH4 kg VS$^{-1}$) | AFR Cumulative Methane Yield (L CH4 kg VS$^{-1}$) | Total Cumulative Methane Yield (L CH4 kg VS$^{-1}$) | Duration to produce 95% methane yield potential (Days) |
|---|---|---|---|---|
| Two-stage | | | | |
| IV.1 | 101 | 192 | 293 | 9.8 |
| IV.2 | 108 | 207 | 315 | 9.2 |
| IV.3 | 138 | 165 | 303 | 7.4 |
| Single/Two-stage | | | | |
| IV.4 | 181 | 138 | 319 | 15.2 |

In Experiments IV.1 and IV.2, sugar beet tailings generated approximately 0.5 g COD/gVS when pre-treated with in-situ method. Only one pass of washing was implemented, generating 12 L of 15 to 17 g/L SCOD strength wash water. The availability of the AFR to process the wash water was dependent the biogasification progression in the SD; precedence was put on AFR sequencing with SD during the start-up stages of biogasification to alleviate accumulation of intermediates. In Experiment IV.1, wash water was processed at the beginning of biogasification (0.7 to 2 days) and after sequencing duties (6.1 to 10.9 days). Wash water treatment in experiment IV.2 was implemented only after AFR sequenced operation with SD was halted. The processing of wash water in the packed bed was conducted at an HRT of 7.5 days in both experiments.

ment of wash water in the AFR decreased to from 8.1 down to 7.4, before leveling off into mid-range pH values (7.4 to 7.8) after four days.

Soluble COD and VFA concentrations in Experiments IV.1 and IV.2 exhibited similar trend behaviors. The SCOD concentrations in the SD increased as high as 10 to 14 g/L during the first three days of biogasification. Upon sequencing, a short lag time (1 to 3 days) was followed by a rapid decay of SCOD; concentrations reduced by 6 g/L SCOD in 3 days, before leveling off to values <8 g/L SCOD. The SCOD levels in the AFR showed an increase only when effluent from SD was treated; concentrations reached as high as 7 g/L SCOD before gradually falling to concentrations as low as 1.3 g/L SCOD within 8 days. Wash water treatment did not contribute to any increases to the SCOD concentration in the AFR. The total VFA concentration in the SD reached as high 2260 and 1600 mg/L within 1 to 3 days in both Experiments IV.1 and IV.2, respectively. Next, the rapid decay of VFA's was observed after a 2-day lag in the sequencing stage, where concentrations fell on average by 1000 to 1500 mg/L within 4 days and leveling off under 500 mg/L at the end of biogasification. The total VFA concentrations in the AFR during sequencing and wash water treatment were maintained below 500 mg/L during the complete duration.

Experiments IV.1 and IV.2 yielded a total cumulative yield of 293 and 315 L $CH_4$ kg $VS^{-1}$, respectively. Approximately 66% of the total cumulative yield in both stages evolved in the AFR and the remaining 34% from the SD; the duration to produced 95% of the total methane potential in both units was in the range of 9.2 to 9.8 days. The two-stage concept of operating at different retention times was exercised; SD and AFR operated at 7.5 and 5 day HRT's, respectively.

In Experiment IV.3, pre-treatment was bypassed on the 3 kg sample of sugar beet tailings. The AFR was sequenced with the SD (at HRT's mentioned in Experiments IV.2 and IV.3) immediately at the start of the run. Unlike Experiments IV.1 and IV.2, the duration to produce 95% of the cumulative methane potential was lower at 7.4 days; the total cumulative methane produced, 303 L CH4 kg $VS^{-1}$. More equal distribution of methane was observed, as 54% of the total cumulative yield evolved from the AFR and 46% from the SD.

From start-up, Experiment IV.3 showed rapid increases in methane production rate and methane fraction in the biogas. In the SD, methane production increased to 1.6 L $L^{-1}$ $d^{-1}$ within 0.5 days and methane composition reached 50% after only 3.5 days of operation. The AFR similarly achieved a max rate of 0.9 $L^{-1}$ $d^{-1}$ after 1 day and reached 60% methane after 1.75 days. As biogasification progressed, the methane production rate in both units declined daily by 0.4 L $L^{-1}$ $d^{-1}$ and the methane composition increased, leveling off at 70% methane. At 4.5 days, 90% of the liquid contents in the SD were sequenced out and replenished by AFR liquid contents; the pH values at this point were both at 8.05. Sequencing was terminated at 6.7 days, as methane production rate in the AFR fell to 0.1 L $L^{-1}$ $d^{-1}$.

Experiment IV.3 SCOD profile increased to 19 g/L SCOD by the first day; the daily SD decay of SCOD in the sequenced stage occurred was 3.1 g/L SCOD. After 6.7 days, the SCOD leveled off just below 5 g/l SCOD. The AFR SCOD concentrations also never exceeded 5 g/L and hovered at 4.5 g/L by end of sequencing. Total VFA concentrations in the SD reached as high as 2200 mg/L in 2.5 days; rapid decay observed in Experiments IV.1 and IV.2 was consistent in Experiment IV.3 as well, where the total VFA concentration fell below 500 mg/L after 7 days of biogasification. The AFR total VFA concentrations were also below 500 mg/L throughout sequencing duration.

Figure 8:
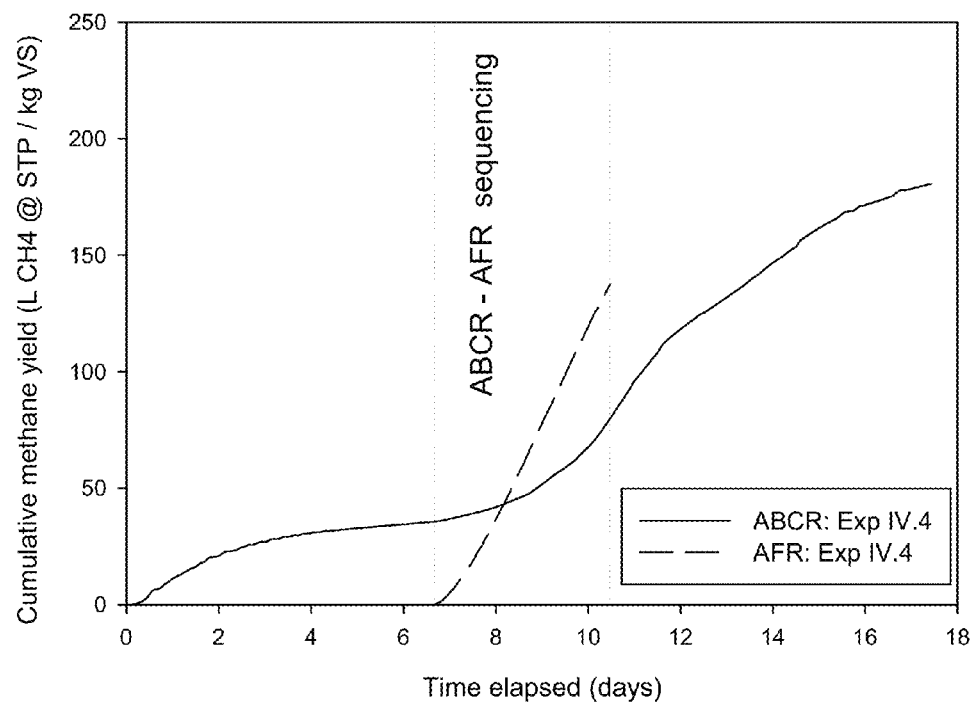
FIG. 8 is a graphical illustration of cumulative methane yields for the liquid and solid reactors used in another embodiment of the two-stage sequential batch anaerobic composting system of the invention.
Figure 9A:
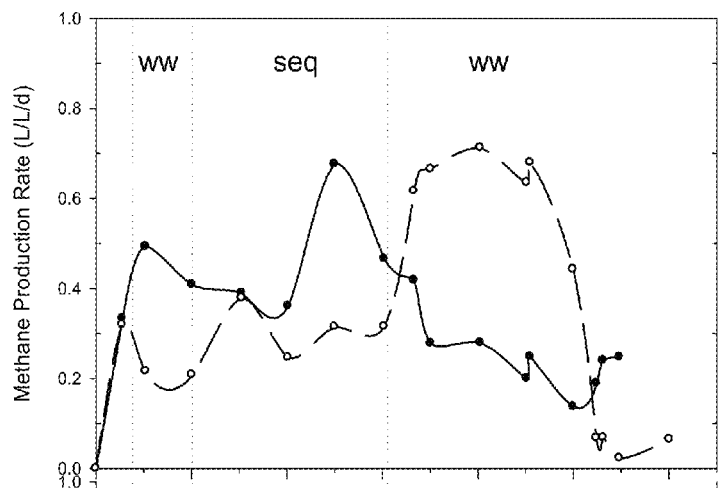
Figure 9B:
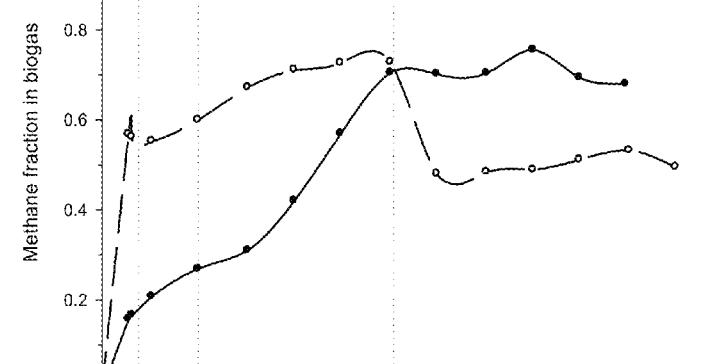
Figure 9C:
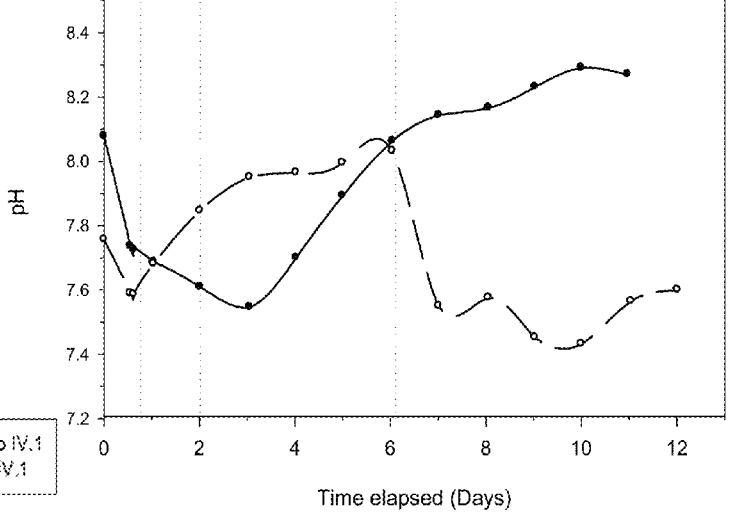
Figure 10A:
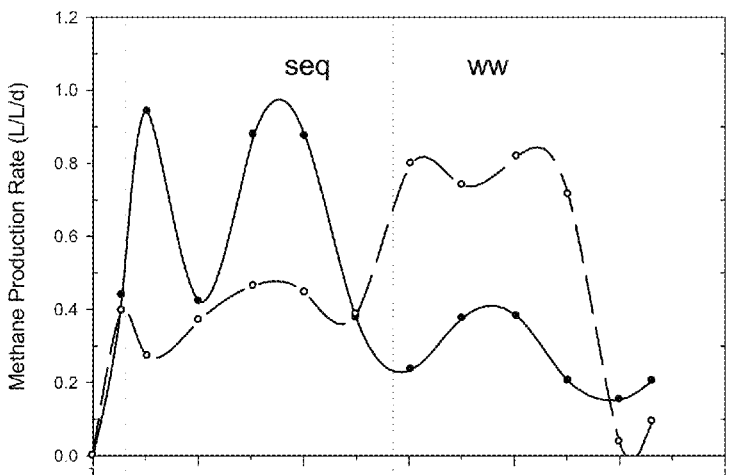
FIGS. 10a-10e are graphical illustrations of various observations derived from the operation of another embodiment of the two-stage sequential batch anaerobic composting system of the invention.
Figure 10B:
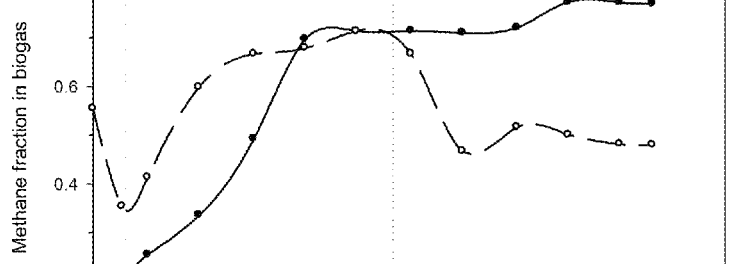
Figure 10C:
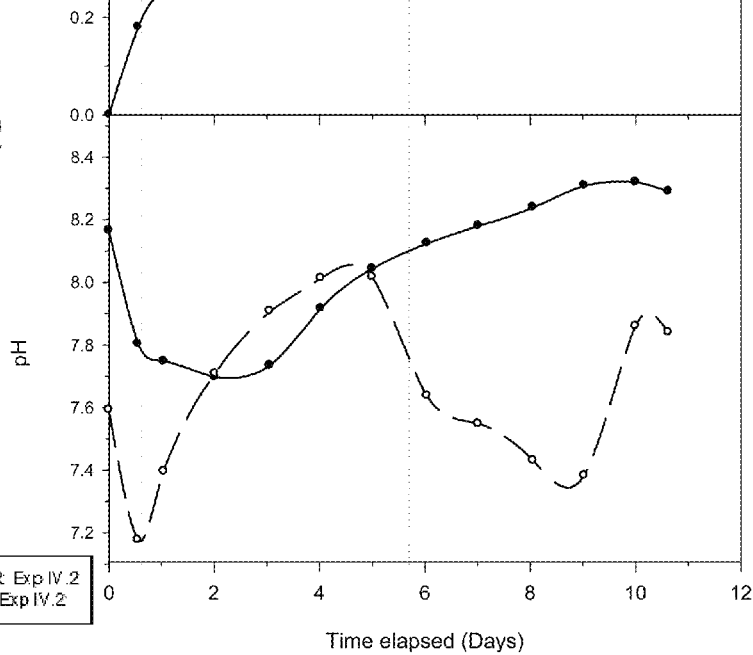
Figure 10D:
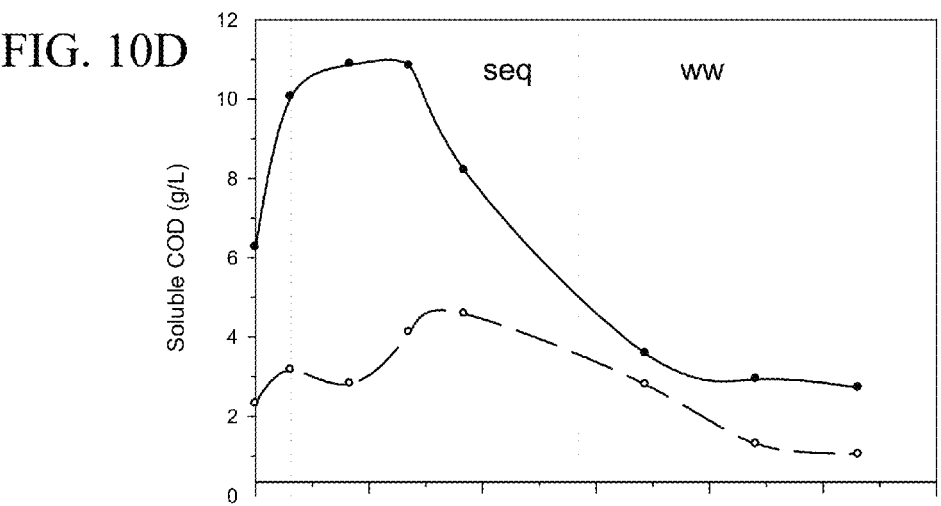
Figure 10E:
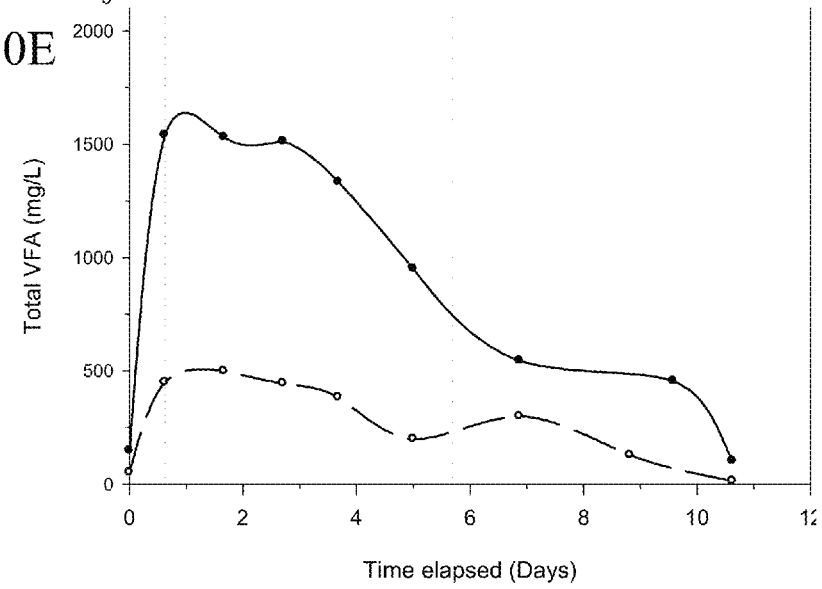
Figure 11D:
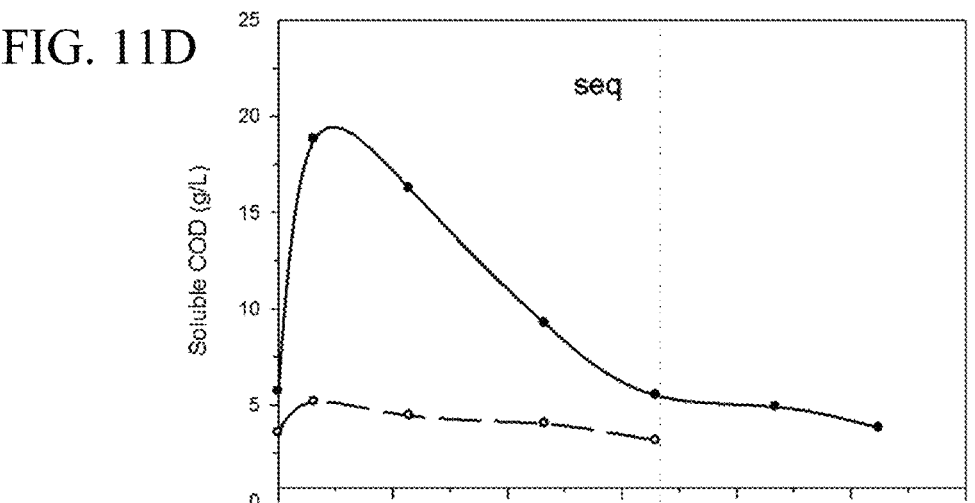
Figure 11E:
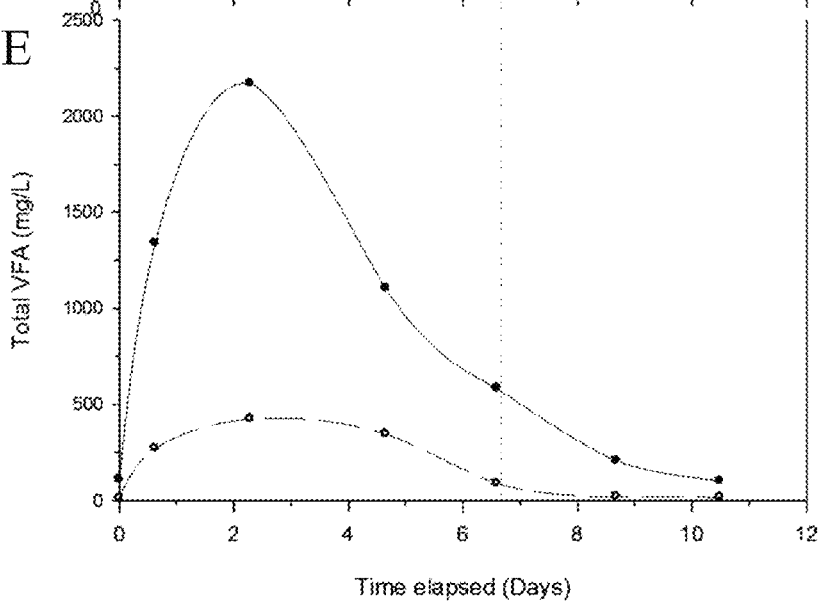
Figure 12A:
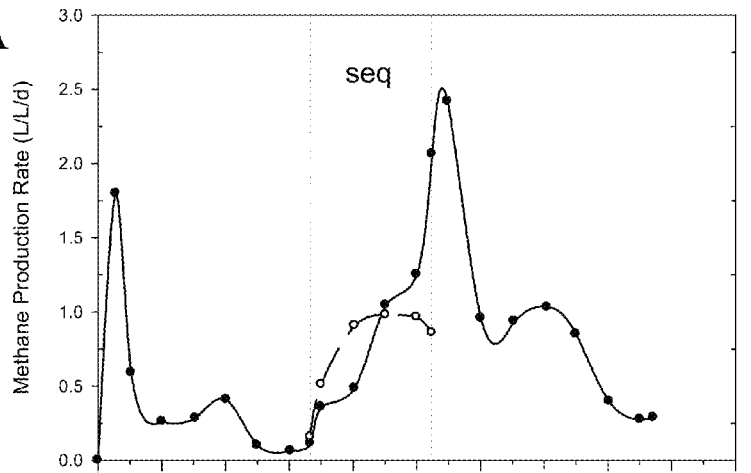
FIGS. 12a-12e are graphical illustrations of various observations derived from the operation of another embodiment of the two-stage sequential batch anaerobic composting system of the invention.
Figure 12B:
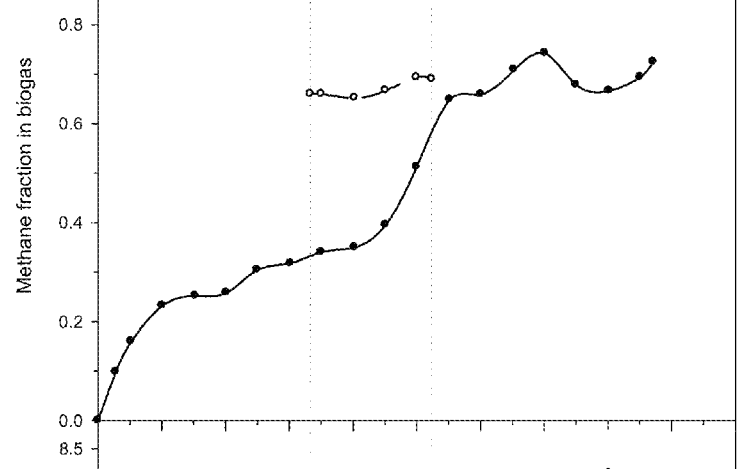
Figure 12C:
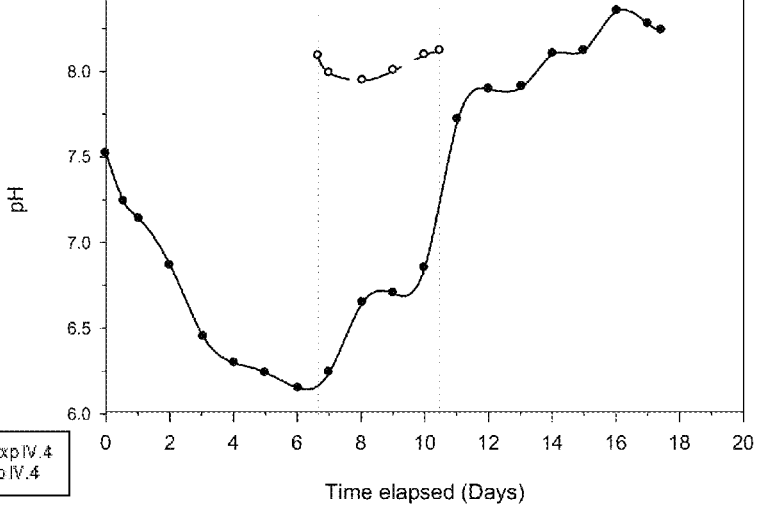
Figure 12D:
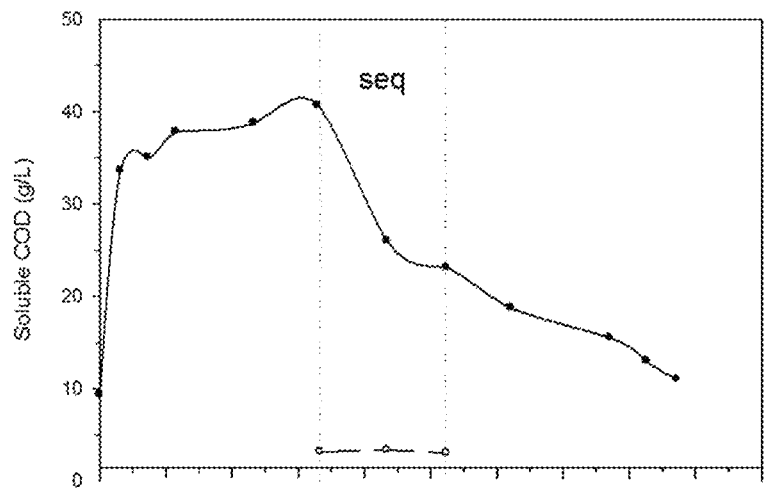
Figure 12E:
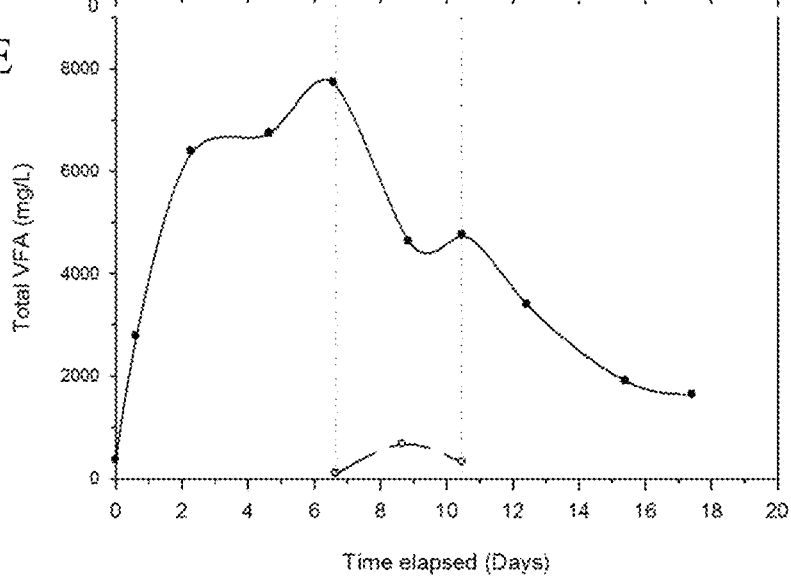

FIGS. 8 and 12 show the biogasification parameter profiles for Experiment IV.4. The accumulation SCOD and VFA intermediates diminished the progression of cumulative methane yield after 6.6 days in single-stage biogasification. In this Study, sequencing with the AFR was conducted between 6.6 days and 10.5 days to revive and activate the pickled reactor. Following a 1.5-day lag, biogasification parameters rapidly increased from day 8 to day 10.5: the methane production rates in the SD increased from 0.5 to 2.5 L $L^{-1}$ $d^{-1}$; the methane composition increased from 35% to 64%; and the pH increased from 6.6 to 7.3. Moreover, the SCOD and VFA profiles during the sequencing duration decreased significantly by 16 g/L and 3000 mg/L, respectively. After the 10.5-day mark, single stage biogasification was re-instated; SCOD and VFA fell to final values of 11 g/L and 1,500 mg/L after 7 days.

The total cumulative methane yield for Experiment IV.4 was experimentally determined as 319 L CH4 kg $VS^{-1}$. Approximately 57% of the total cumulative yield in both stages evolved in the SD and the remaining 43% from the AFR; the duration to produced 95% of the total methane potential in both units was 15.2 days. A sequencing duration of only 3.8 days was applied towards reviving the inhibited single-stage experiment aforementioned.

V. Discussion

The problems associated with volatile fatty acids and high levels of soluble COD were previously shown to impede the rates of degradation. Implementing a two-stage operation for the biogasification of sugar beet tailings in this Study translated to enhancing the rate at which accumulated constituents (SCOD and VFA) where removed and degraded; the AFR provided the necessary replenishment of micro-organisms, and buffer necessary for methanogenic start-up support in the SD reactor; it did not rely on a certain percentage of digested residue Increases in the TS and VS reduction in this Study confirmed that a substantial portion of degradable matter residing in the liquid was capable of being degraded further. From previous un-bulked experiments, a VS reduction of 85 ±1% did not coincide with the total measured cumulative methane yield, 258±27 L CH4 kg $VS^{-1}$; effluent solid recovery was shown to un-account for 12% of un-degraded VS. In un-bulked sequenced Experiments IV.1 to IV.3, the discrepancy between the total experimentally measured yield and % VS reduction was greatly reduced. The average experimental cumulative methane yield measured was 304±11 L CH4 kg $VS^{-1}$, which theoretically corresponded to 88±2% VS reduction; residue VS analysis for Experiments IV.1 to IV.3 yielded 88±2% VS reduction. It is speculated that sequencing increased the retention of contributing constituents within the AFR that would otherwise not break down as rapidly in a single-stage solids reactor; total suspended solids in wash water and VS locked-up in reactor liquor were mineralized to methane more readily. Further evidence of increased degradation was indicated by the SCOD profiles in both SD and AFR, where accumulated concentrations returned or fell below the typical starting values (5 g/L).

The effect of sequencing in Experiments IV.1 and IV.2 circumvented the sluggish behavior observed in previous studies between the second and the fourth day. Methane production rate was increased by 0.2 L $L^{-1}$ $d^{-1}$ and yield was improved by 10 L kg $VS^{-1}$ $d^{-1}$ when sequenced. It is suspected that the balance between acidogenic and methanogenic groups in the SD during that time was improved by addition of microorganisms and removal of VFA's and SCOD. Experiment IV.3 showed that pre-treatment was not a necessary step implementing two-stage operation with the AFR used in the research work. At a peak organic loading rate of 2.5 g COD $L^{-1}$ on the first day of sequencing, the AFR's methane production rate increased to 0.9 L $L^{-1}$ $d^{-1}$ with no signs of sluggish behavior. In Experiment IV.4, the organic loading rate delivered varied between 5.3 and 3.3 g COD $L^{-1}$ $d^{-1}$ for the first two days of sequencing. The AFR sustained a methane production rate of 0.9 L $L^{-1}$ $d^{-1}$ and VFA concentrations climbed to 670 mg/L before falling below 500 mg/L. Thus, the AFR demonstrated its potential to effectively treat effluents between 5 to 40 g/L at an HRT of 7.5 days without major complications during sequencing.

When compared against prior sequential batch anaerobic composting, also known as SEBAC systems (Teixeira et al., 2005, Space-based SEBAC-II solid waste management technology for commercial application to beet sugar industry. Paper No. 2005-01-3026. Proceedings of International Conference on Environmental Systems (ICES) and European Symposium on Space Environmental Control Systems, July 11-14, Rome Italy), the spent digester in a flooded mesophilic SEBAC-2 showed poor performance because of the process' inability to treat the high amount of readily soluble organic compounds that foimed initially. In a SEBAC process, the leachate re-circulation strategy ensures that readily soluble COD generated in a fresh waste bed ($1^{st}$ stage) would be converted to methane in the second stage and that microorganisms, buffer and nutrients would be recycled back; this was contingent on the basis that a significant amount of residue remains in the mature reactor, harboring the necessary microorganisms to carry-out degradation of incoming intermediates (Chynoweth et al., 2002, Anaerobic composting for recovery of nutrients, compost, and energy from solid wastes during space missions. Paper No. 2002-01-2351. International Conference on Environmental Systems (ICES)).

In contrast, the AFR used in this Study was independent of feedstock residue; it provided a consistent centralized treatment option that can handle high SCOD liquor from a solids reactor. Of note, thermophilic operation appears to be a factor in improving the rates of degradation in the two-stage implemented in this work.

The concept of running two-stage sequential batch biogasification on sugar beet tailings with a high-rate anaerobic wastewater reactor suggests that pre-treatment could be avoided and that higher bulking densities may be afforded in the first stage. The physical limitations of trapped biogas that may limit the efficiency of the first SD reactor are addressed utilizing the cross flow baffles described herein. Experiment IV. 3, which had an in-vessel bulking density of 75 kg/m³ (dry basis), occupied 83% of the working volume. Therefore, the savings in pre-treatment on account of incorporating the AFR as a supporting unit process to the treatment of raw sugar beet tailings was a considerable accomplishment. High rate systems such as anaerobic filter (AF) or Hybrid UASB/AF are known to treat wastewaters >5 g COD $L^{-1}$ $d^{-1}$. Thus, practical outlooks of increasing the compaction density and attaining high degradation of sugar beet tailings seem promising.

The experiments described herein demonstrate beneficial cumulative methane potential and VS reduction when utilizing the combined two-stage SD/AFR system for the biogasification of sugar beet tailings, which were found to be 304 L kg $VS^{-1}$ and 88±2%, respectively. On average, the overall methane yield contributions of the SD and AFR during two-stage operation were 116 L $CH_4$ kg $VS^{-1}$ (38%) and 188 L $CH_4$ kg $VS^{-1}$ (62%), respectively. The recovery of a single-stage inhibited reactor was fulfilled by sequencing with the AFR at an HRT of 7.5 days; cumulative methane yield and VS reduction for 5 kg of un-washed sugar beet tailings were 319 L kg $VS^{-1}$ and 93%. Finally, expulsion of a pre-treatment step to remove readily soluble fraction of tailings was justified by the AFR's ability to process organic loading rates between 2.5 and 5.3 g COD $L^{-1}$ $d^{-1}$. This resulted in reducing the total process time by 0.5-1 days. Accordingly, the subject two-stage system using sequencing between a solid and liquid reactor was shown to decrease the duration to produce 95% of the methane yield in less than 10 days consistently.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A continuous feed anaerobic digester system for converting degradable solid waste feedstock into useful materials, wherein the system comprises:
    at least one single stage anaerobic reactor for treating a solid waste stream (SD reactor);
    at least one single-stage anaerobic reactor for treating soluble components in waste water separated from solid waste stream (AFR reactor); and
    at least one conduit connecting the SD reactor to the AFR reactor;
    wherein the SD reactor comprises at least one horizontally-oriented cross-flow baffle, wherein the cross-flow baffle comprises an elongate body composed of two side walls and a top section that is substantially not flat to deflect solid material present in the reactor from settling on the top section,
    wherein the side walls comprise a permeable material, and
    wherein the baffle further comprises a channel that runs parallel along the elongate body of the baffle, wherein the channel injects and/or withdraws liquid to and/or from the side walls via at least one fluid pump.

2. The digester system of claim 1, wherein the top section of the cross-flow baffle comprises a first top side face and an opposing second to side face that together form an inverted substantially V-shaped transverse cross section that partially bounds a collection channel for at least one gas produced in the SD reactor.

3. The digester system of claim 1, wherein the permeable material is a mesh material having a pore size that is dependent on solid material present in the reactor and the desired flow rates of the waste water and/or waste stream.

4. The digester system of claim 3, wherein the mesh material has a pore size of approximately 100 microns.

5. The digester system of claim 3, wherein the permeable material comprises metal, ceramic, or polymer materials; or any combinations thereof.

6. The digester system of claim 3, wherein the permeable material is a mesh material having a pore size up to 250 microns.

7. The digester system of claim 6, wherein the permeable material comprises at least one of the following materials: rubber, cloth, hair and/or plastic.

8. The digester system of claim 1, wherein two or more channel(s) are provided to inject and/or withdraw liquid to and/or from the side walls via the at least one fluid pump.

9. The digester system of claim 1, wherein the solid waste stream comprises less than about 55% total solid waste.

10. The digester system of claim 9, wherein the solid waste stream comprises about 35% to 45% total solid waste.

11. The digester system of claim 9, wherein the solid waste stream comprises about 20% to about 35% total solid waste.

12. The digester system of claim 1, wherein the SD and/or AFR reactor comprises at least one port for collecting at least one gas produced in the reactor(s).

13. The digester system of claim 1, wherein the solid waste stream and/or the SD reactor and/or the AFR reactor comprises a bulking agent.

14. The digester system of claim 13, wherein the bulking agent comprises one or more of any combination of the following: coal, stones, and/or rocks.

15. The digester system of claim 13, wherein the bulking agent comprises one or more of any combination of the following: metal objects, gravel, plastic materials, yard trimming waste, cardboard, expanded clay, wood chips, sawdust, animal bedding, biosolids, and hair.

16. The digester system of claim 13, wherein the bulking agent is compatible with a solid waste stream.

17. The digester system of claim 1, wherein the solid waste stream comprises carbonaceous organic waste.

18. The digester system of claim 17, wherein the carbonaceous organic waste comprises any one or combination of the following: sewage sludge, forestry waste, food waste, agricultural waste, municipal waste, and /or yard/garden waste.

19. The digester system of claim 17, wherein the solid waste stream is raw feed.

20. The digester system of claim 1, wherein a plurality of cross-flow baffles are provided in the SD reactor and/or AFR reactor.

21. The digester system of claim 1, further comprising a means for controlling the temperature of a reactor, wherein the means for controlling the temperature of the reactor comprises at least one of the following: a solar water heater, a gas-powered water heater, a steam generator, and/or a heat exchanger.

22. The digester system of claim 1, further comprising a means for controlling the temperature of a reactor, wherein the means for controlling the temperature of the reactor comprises at least one of the following: a heater or a heat generator.

23. The digester system of claim 1, wherein the SD reactor further comprises at least one sealed entry and at least one sealed egress.

24. The digester system of claim 23, wherein the at least one sealed entry is at the top of the SD reactor and the at least one sealed egress is at the bottom of the SD reactor.

25. The digester system of claim 23, wherein the at least one sealed entry and/or the at least one sealed egress comprises a rotary valve.

26. The digester system of claim 23, wherein the at least one sealed entry and/or the at least one sealed egress is located at a top, a bottom, a side or sides of the SD reactor.

27. The digester system of claim 23, wherein the at least one sealed entry and/or the at least one sealed egress comprises at least one of the following: a staged valve, rotary lobe pump, and/or other positive displacement pump.

28. The digester system of claim 1, wherein the AFR reactor comprises a media material capable of supporting anaerobic bacteria.

29. The digester system of claim 28, wherein the media material comprises:
rubber, plastic, wood, or metal.

30. The digester system of claim 28, wherein the media material is a semi-rigid, high-density polyethylene plastic mesh sheet having a mesh size of approximately 1×1 or 2×2 inches.

31. The digester system of claim 28, wherein the media material comprises at least one of the following materials: rock, activated carbon, expanded clay, tire chips, fabrics, coal or stone.

32. The digester system of claim 1, wherein the SD and/or the AFR reactor produces at least one gas.

33. The digester system of claim 32, wherein the at least one gas comprises methane.

34. The digester system of claim 32, wherein the at least one gas comprises hydrogen and/or carbon dioxide.

* * * * *

UNITED STATES PATENT AND TRADEMARK OFFICE
CERTIFICATE OF CORRECTION

PATENT NO.        : 8,962,310 B2                                              Page 1 of 1
APPLICATION NO.   : 13/803218
DATED             : February 24, 2015
INVENTOR(S)       : Pratap Pullammanappallil It is certified that error appears in the above-identified patent and that said Letters Patent is hereby corrected as shown below:

In the Specification

Column 3,
Line 15, ""foaming"" should read --"foaming."--.

Column 10,
Line 29, "bio as" should read --biogas--.

Column 10,
Line 48, "angle a" should read --angle α--.

Column 18,
Line 31, "88±2%" should read --88 ± 4%--.

Column 18,
Line 53, "2.5 g COD $L^{-1}$ on" should read --2.5 g COD $L^{-1}$ $d^{-1}$ on--.

Column 19,
Line 3, "Rome Italy)," should read --Rome, Italy),--.

In the Claims

Column 20,
Line 28, "to side" should read --top side--.

Signed and Sealed this
Twenty-second Day of September, 2015

Michelle K. Lee
*Director of the United States Patent and Trademark Office*